(12) United States Patent
Belhe et al.

(10) Patent No.: US 8,702,641 B2
(45) Date of Patent: Apr. 22, 2014

(54) GASTROINTESTINAL PROSTHESES HAVING PARTIAL BYPASS CONFIGURATIONS

(75) Inventors: Kedar R. Belhe, Minnetonka, MN (US); Paul J. Thompson, Minnetonka, MN (US)

(73) Assignee: MetaModix, Inc., Plymouth, MN (US)

( * ) Notice: Subject to any disclaimer, the term of this patent is extended or adjusted under 35 U.S.C. 154(b) by 149 days.

(21) Appl. No.: 12/986,268

(22) Filed: Jan. 7, 2011

(65) Prior Publication Data
US 2011/0106273 A1     May 5, 2011

Related U.S. Application Data

(63) Continuation-in-part of application No. 12/833,605, filed on Jul. 9, 2010, now Pat. No. 8,211,186, and a continuation-in-part of application No. 12/752,697, filed on Apr. 1, 2010, now Pat. No. 8,282,598.

(60) Provisional application No. 61/335,472, filed on Jan. 7, 2010, provisional application No. 61/211,853, filed on Apr. 3, 2009, provisional application No. 61/270,588, filed on Jul. 10, 2009.

(51) Int. Cl.
*A61B 19/00*     (2006.01)

(52) U.S. Cl.
USPC ............................................... 604/8; 604/19

(58) Field of Classification Search
None
See application file for complete search history.

(56) References Cited

U.S. PATENT DOCUMENTS

| | | |
|---|---|---|
| 4,134,405 A | 1/1979 | Smit |
| 4,204,530 A | 5/1980 | Finney |
| 4,246,893 A | 1/1981 | Berson |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |

(Continued)

FOREIGN PATENT DOCUMENTS

| | | |
|---|---|---|
| AU | 2006227471 B2 | 9/2006 |
| CN | 1618411 A | 5/2005 |

(Continued)

OTHER PUBLICATIONS

International Search Report and Written Opinion issued in PCT/US2010/029648, mailed Aug. 24, 2010.

(Continued)

*Primary Examiner* — Leslie Deak
*Assistant Examiner* — Sara Sass
(74) *Attorney, Agent, or Firm* — Faegre Baker Daniels LLP

(57) ABSTRACT

A system of components may be used separately or in combination to create partial bypass of food, stomach and intestinal secretions and digestive enzymes. The systems are designed to be modular so as to allow the physicians to quickly replace certain elements to tailor the amount of material bypassed, the restriction applied to food passage, and the origin and destination of bypass according to the patient's individualized clinical needs.

19 Claims, 20 Drawing Sheets

(56) References Cited

U.S. PATENT DOCUMENTS

| | | |
|---|---|---|
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,749,921 A | 5/1998 | Lenker et al. |
| 5,753,253 A | 5/1998 | Meyer |
| 5,820,584 A | 10/1998 | Crabb |
| 6,017,563 A | 1/2000 | Knight et al. |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | Delegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | Delegge |
| 7,306,614 B2 | 12/2007 | Weller et al. |
| 7,314,489 B2 | 1/2008 | Mckenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr et al. |
| 7,569,056 B2 | 8/2009 | Cragg et al. |
| 7,601,178 B2 | 10/2009 | Imran et al. |
| 7,608,114 B2 | 10/2009 | Levine et al. |
| 7,608,578 B2 | 10/2009 | Miller et al. |
| 7,618,435 B2 | 11/2009 | Opolski et al. |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,114,045 B2 | 2/2012 | Surti |
| 8,211,186 B2 | 7/2012 | Belhe et al. |
| 8,282,598 B2 | 10/2012 | Belhe et al. |
| 2002/0183768 A1 | 12/2002 | Deem et al. |
| 2002/0188354 A1 | 12/2002 | Peghini et al. |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1* | 5/2004 | Kagan et al. ............... 604/264 |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |

(56) References Cited

U.S. PATENT DOCUMENTS

| | | |
|---|---|---|
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2012/0065571 A1 | 3/2012 | Thompson et al. |
| 2012/0184893 A1 | 7/2012 | Thompson et al. |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2013/0030351 A1 | 1/2013 | Belhe et al. |

FOREIGN PATENT DOCUMENTS

| | | |
|---|---|---|
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1520528 A2 | 4/2005 |
| EP | 1555970 A1 | 7/2005 |
| EP | 1569582 A2 | 9/2005 |

(56) References Cited

FOREIGN PATENT DOCUMENTS

| | | |
|---|---|---|
| EP | 1585458 A1 | 10/2005 |
| EP | 1585460 A1 | 10/2005 |
| EP | 1603488 A2 | 12/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1768618 A1 | 4/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 | 9/2007 |
| EP | 1850811 A1 | 11/2007 |
| EP | 1850812 A1 | 11/2007 |
| EP | 1881781 A2 | 1/2008 |
| EP | 1883370 A2 | 2/2008 |
| EP | 1887995 A2 | 2/2008 |
| EP | 1895887 A2 | 3/2008 |
| EP | 1933721 A1 | 6/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1610719 B1 | 1/2010 |
| WO | WO 98/49943 | 11/1998 |
| WO | WO 02/096327 | 12/2002 |
| WO | WO 03/017882 | 3/2003 |
| WO | WO 03/086246 | 10/2003 |
| WO | WO 03/086247 | 10/2003 |
| WO | WO 03/094785 | 11/2003 |
| WO | WO 2004/011085 | 2/2004 |
| WO | WO 2004/017863 | 3/2004 |
| WO | WO 2004/041133 | 5/2004 |
| WO | WO 2004/049982 | 6/2004 |
| WO | WO 2004/064680 | 8/2004 |
| WO | WO 2004/064685 | 8/2004 |
| WO | WO 2004/087014 | 10/2004 |
| WO | WO 2004/087233 | 10/2004 |
| WO | WO 2005/037152 | 4/2005 |
| WO | WO 2005/058415 | 6/2005 |
| WO | WO 2005/060869 | 7/2005 |
| WO | WO 2005/060882 | 7/2005 |
| WO | WO 2005/065412 | 7/2005 |
| WO | WO 2005/097012 | 10/2005 |
| WO | WO 2005/099591 | 10/2005 |
| WO | WO 2005/110244 | 11/2005 |
| WO | WO 2005/110280 | 11/2005 |
| WO | WO 2005/112822 | 12/2005 |
| WO | WO 2005/120363 | 12/2005 |
| WO | WO 2006/014496 | 2/2006 |
| WO | WO 2006/016894 | 2/2006 |
| WO | WO 2006/020370 | 2/2006 |
| WO | WO 2006/028898 | 3/2006 |
| WO | WO 2006/034062 | 3/2006 |
| WO | WO 2006/060049 | 6/2006 |
| WO | WO 2006/062996 | 6/2006 |
| WO | WO 2006/078781 | 7/2006 |
| WO | WO 2006/078927 | 7/2006 |
| WO | WO 2006/102012 | 9/2006 |
| WO | WO2006102240 A2 | 9/2006 |
| WO | WO 2006/124880 | 11/2006 |
| WO | WO 2006/127593 | 11/2006 |
| WO | WO 2006/133311 | 12/2006 |
| WO | 2007019117 | 2/2007 |
| WO | WO 2007/030829 | 3/2007 |
| WO | WO 2007/038715 | 4/2007 |
| WO | WO 2007/041598 | 4/2007 |
| WO | WO 2007/075396 | 7/2007 |
| WO | WO 2007/092390 | 8/2007 |
| WO | WO 2007/107990 | 9/2007 |
| WO | WO 2007/127209 | 11/2007 |
| WO | WO 2007/136468 | 11/2007 |
| WO | WO 2007/139920 | 12/2007 |
| WO | WO 2007/142829 | 12/2007 |
| WO | WO 2007/142832 | 12/2007 |
| WO | WO 2007/142833 | 12/2007 |
| WO | WO 2007/142834 | 12/2007 |
| WO | WO 2007/145684 | 12/2007 |
| WO | WO 2008/005510 | 1/2008 |
| WO | WO 2008/030403 | 3/2008 |
| WO | WO 2008/033409 | 3/2008 |
| WO | WO 2008/033474 | 3/2008 |
| WO | WO 2008/039800 | 4/2008 |
| WO | WO 2008/101048 | 8/2008 |
| WO | WO 2008/106041 | 9/2008 |
| WO | WO 2008/106279 | 9/2008 |
| WO | WO 2008/112942 | 9/2008 |
| WO | WO 2008/127552 | 10/2008 |
| WO | WO 2008/141288 | 11/2008 |
| WO | WO 2008/148047 | 12/2008 |
| WO | WO 2008/150905 | 12/2008 |
| WO | WO 2008/154450 | 12/2008 |
| WO | WO 2008/154594 | 12/2008 |
| WO | WO 2009/011881 | 1/2009 |
| WO | WO 2009/011882 | 1/2009 |
| WO | WO 2009/012335 | 1/2009 |
| WO | WO 2009/036244 | 3/2009 |
| WO | WO 2009/046126 | 4/2009 |
| WO | WO 2009/082710 | 7/2009 |
| WO | WO 2009/085107 | 7/2009 |
| WO | WO 2009/086549 | 7/2009 |
| WO | WO 2009/097582 | 8/2009 |
| WO | WO 2009/097585 | 8/2009 |
| WO | WO2010115011 A1 | 10/2010 |
| WO | WO2011062882 A1 | 5/2011 |
| WO | WO 2011073970 A1 | 6/2011 |
| WO | WO2011099940 A8 | 8/2011 |

OTHER PUBLICATIONS

Invitation to Pay Additional Fees issued in PCT/US2010/029648, mailed Jun. 1, 2010.

Vetter, Marion et al., "Narrative Review: Effect of bariatric Surgery on Type 2 Diabetes Mellitus", Annals of Internal Medicine, Jan. 20, 2009, 150(2), pp. 94-104.

Buchwald, Henry et al., "Bariatric Surgery: A Systematic Review and Meta-Analysis", JAMA, Oct. 13, 2004, 292(14), pp. 1724-1737.

Rubino, Francesco et al., "Potential of Surgery for Curing Type 2 Diabetes Mellitus", Annals of Surgery, Nov. 2002, 236(5), 554-559.

Cummings, David E. et al., "Role of the bypassed proximal intestine in the anti-diabetic effects of bariatric surgery", Surgery for Obesity and Related Diseases 3 2007, pp. 109-115.

Strader, April et al., "Weight Loss Through Ileal transposition is accompanied by increased ileal hormone secretion and synthesis in rats", Am J Physiol Endocrinol Metab 288: E447-E453, 2005.

Troy, Stephanie et al., "Intestinal Gluconeogenesis is a key factor for early metabolic changes after gastric bypass but not after gastric lap-band in mice", Cell metabolism 8, 201-211, Sep. 3, 2008.

Rodriguez-Grunert, Leonardo et al., "First Human Experience With endoscopically Delivered and retrieved duodenal-jejunal bypass sleeve", Surgery for Obesity and Related diseases 4 (2008) 55-59.

Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.

Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.

(56) References Cited

OTHER PUBLICATIONS

International Search Report and Written Opinion issued in PCT/US2010/041574, mailed Jan. 25, 2011.
International Search Report and Written Opinion issued in PCT/US2011/061193.
International Search Report and Written Opinion issued in PCT/US2011/020560, mailed Mar. 28, 2011, 10 pages.
International Search Report and Written Opinion issued in PCT/US2012/023048, mailed Jun. 22, 2012.
International Search Report and Written Opinion issued in PCT/US12/58202, mailed Jan. 23, 2013, 14 pages.

* cited by examiner

GASTROINTESTINAL PROSTHESES HAVING PARTIAL BYPASS CONFIGURATIONS

CROSS-REFERENCE TO RELATED APPLICATIONS

This application claims the benefit under 35 U.S.C. §119(e) to U.S. provisional patent application 61/335,472, filed Jan. 7, 2010, entitled "Apparatus and Methods for Customized and Partial Intraluminal Bypass Procedures," which is herein incorporated by reference in its entirety. This application is a continuation-in-part of each of the following applications: U.S. patent application Ser. No. 12/752,697, filed Apr. 1, 2010, which claims the benefit of U.S. provisional patent application 61/211,853, filed Apr. 3, 2009; and U.S. patent application Ser. No. 12/833,605, filed Jul. 9, 2010, which claims the benefit of U.S. provisional patent application 61/270,588, filed Jul. 10, 2009, the disclosures of which are each hereby incorporated by reference in their entirety.

TECHNICAL FIELD

This invention generally relates to implants placed within gastrointestinal systems, including the esophagus, the stomach, and the intestines. In particular, it relates to implant systems having components implantable and removable using laparoscopic and endoscopic techniques for treatment of obesity, diabetes, reflux, and other gastrointestinal conditions.

BACKGROUND

Bariatric surgery procedures, such as sleeve gastrectomy, the Rouen-Y gastric bypass (RYGB), and the biliopancreatic diversion (BPD), modify food intake and/or absorption within the gastrointestinal system to effect weight loss in obese patients. These procedures affect metabolic processes within the gastrointestinal system, by either short-circuiting certain natural pathways or creating different interaction between the consumed food, the digestive tract, its secretions and the neuro-hormonal system regulating food intake and metabolism. In recent years, there has been a growing clinical consensus that obese diabetic patients who undergo bariatric surgery see remarkable resolution of their Type-2 Diabetes Mellitus (T2DM) soon after the procedure. The remarkable resolution of diabetes after RYGB and BPD typically occurs too fast to be accounted for by weight loss alone, suggesting that there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there is an increasing amount of ongoing effort to develop minimally invasive procedures to mimic the effects of bariatric surgery using minimally invasive procedures. One such procedure involves the use of gastrointestinal implants that modify transport and absorption of food and organ secretions. For example, U.S. Pat. No. 7,476,256 describes an implant having a tubular sleeve with an anchor having barbs. While these implants may be delivered endoscopically, the implants offer the physician limited flexibility and are not readily removable or replaceable, as the entire implant is subject to tissue in-growth after implantation. Moreover, stents with active fixation means, such as barbs that penetrate into the surrounding tissue, may potentially cause tissue necrosis and erosion of the implants through the tissue, which can lead to serious complications such as systemic infection. Also, due to the intermittent peristaltic motion within the digestive tract, implants such as stents have a tendency to migrate.

SUMMARY

According to various embodiments, the present invention is a partial gastrointestinal implant system for treating metabolic disorders, such as diabetes and obesity. According to some embodiments, the system includes an anchoring element (e.g., stents, rings, fabric, or elastomeric cuffs) with sleeve or graft extensions, anchored within the gastrointestinal system (e.g., the esophagus, the gastro-esophageal junction, the pyloric junction, the duodenum, the jejunum, and/or the ileum), the anchoring element including docking capability, and tubular implants (e.g., thin sleeves or stent grafts) configured to be reversibly attached to the anchoring element. According to some embodiments, the system allows attachment of one or multiple tubular implants to the gastrointestinal anchoring element. According to some embodiments, the cross-section area of the implants can be varied or adjusted, such that systems can be created where food or secretions entering the proximal portion of the system can be selectively channeled to alternate destinations, thereby creating customized and partial bypass systems. By adjusting the sizing of the sleeves and the restrictive elements in the system, this procedure can also simulate mechanisms of restrictive surgical procedures.

According to various embodiments, the present invention is a modular intra-luminal implant system for treating metabolic disorders such as obesity and diabetes, which provides far more flexible therapy alternatives than single devices to treat these disorders. These implant systems include components that can be selectively added or removed to mimic a variety of bariatric surgical procedures with a single basic construct. The fundamental building blocks of the system include anchoring implants that are placed within the GI system or some instances around particular organs. These low-profile implants are designed for long-term performance with minimal interference with normal physiological processes. Features of these anchoring implants allow them to act as docking stations for therapy implants designed for achieving certain metabolic modification goals. By using a combination of anchoring implants with corresponding replaceable tubular elements that dock with them, it is possible to design therapies with particular metabolic modification goals or those that mimic currently practiced bariatric surgical procedures. This allows the physician to customize the therapy to the patient at the time of the initial procedure but also allows the flexibility to alter the therapy during the lifetime of the patient by replacing individual components.

According to some embodiments, the modular systems of the invention includes an anchoring implant portion (docking element) including an expandable structure (e.g., a low profile stent or ring or fabric/elastomeric cuff) anchored within the esophagus, the gastro-esophageal junction, the pyloric junction, the duodenum or the jejunum and may have sleeve or graft extensions. The stents may be balloon expandable or self-expanding and anchor against the tissue with radial force. The rings could be made of self-expanding nitinol and anchor to the tissue by entrapment of the tissue within the ring elements or by radial force. The cuffs could be either sutured or stapled or permanently or reversibly attached by other mechanical means to the tissue. The anchoring implant includes or is adapted to receive (e.g., endoscopically) features that enable docking functionality. The docking functionality of the stent, ring or cuff, for example, could take the form of magnetic elements, hooks, mating mechanical elements or structures (e.g., the stent braid or mesh or corresponding hook and loop structures) that are integral to the framework of the stent, ring or cuff or the sleeve or graft extension. The system also could be such that the docking functionality is not integral to the stent, ring or cuff but is introduced later by attaching other elements such as magnets, hooks, mating mechanical elements, etc. to the framework of the stent, ring, cuff or to the sleeve/graft extension of the above implants. Therapeutic implants, such as tubular sleeves or stent grafts, are adapted to be reversibly attached to the anchoring implants. These therapeutic implants will have corresponding features (e.g., magnets, hooks, mechanical elements) to enable docking to the anchoring implants, so that the therapeutic implants can be reversibly attached to the anchoring implants. In some embodiments, the tubular implants will not be in contact with tissue to minimize or prevent tissue in-growth and facilitate easy removal with endoscopic instrumentation after long-term implantation.

The present invention, according to various embodiments, includes a modular gastrointestinal implant system for treating metabolic disorders such as diabetes and obesity by creating partial internal bypasses of food and organ secretions within the gastro-intestinal tract. The system includes low-profile anchoring implants that are affixed within the stomach, the esophagus, the intestine (or at internal junctions of these organs) or around these organs and enable secure attachment of (i.e., act as docking elements for) other implants; and other implants whose design facilitates partial internal by-pass of food and organ secretions from one site within the gastro-intestinal tract to other sites within the gastro-intestinal tract (partial bypass elements) that are attached to these anchoring implants. In some embodiments, the low-profile implant is a stent-graft or a stent with a sleeve element. In some embodiments, the low-profile implant is a fabric or elastomeric cuff. In some embodiments, the low-profile implants are stents divided into multiple channels. In some embodiments, the low-profile implants are multi-limb stent-grafts.

According to various embodiments, the present invention is a method for treating metabolic disorders such as diabetes and obesity consisting of (a) placing low-profile implants that can be affixed within the stomach, the esophagus, the intestine or at internal junctions of these organs or around these organs and (b) securely attaching other gastro-intestinal implants that permit partial internal by-pass of food and organ secretions from one site within the gastro-intestinal tract to other sites within the gastro-intestinal tract, to these low-profile implants.

According to various embodiments, the present invention is a method for creating a reversible treatment for metabolic disorders such as diabetes and obesity consisting of (a) placing low-profile implants that can be affixed within the stomach, the esophagus, the intestine or at internal junctions of these organs or around these organs and (b) placing other gastro-intestinal implants that permit partial internal by-pass of food and organ secretions from one site within the gastro-intestinal tract to other sites within the gastro-intestinal tract, to these low-profile implants and not to the tissue so that the procedure can be reversed easily.

According to various embodiments, the present invention is a modular system for selectively restricting passage of food and organ secretions within the gastro-intestinal tract that consists of (a) low-profile implants that are affixed within the stomach, the esophagus, the intestine or at internal junctions of these organs or around these organs and which enable secure attachment of other implants (docking elements) and (b) other gastro-intestinal implants whose design facilitates selective restriction of passage of food and organ secretions from one site within the gastro-intestinal tract to other sites within the gastro-intestinal tract that are attached to these permanent implants (restrictive bypass elements). In some embodiments, the structure or design feature of the implant that enables secure attachment of one or more implants to it consists of a double-braid with hollow space between the two braids.

According to various embodiments, the present invention is a method for treating metabolic disorders such as diabetes and consisting of (a) placing low-profile implants that can be affixed within the stomach, the esophagus, the intestine or at internal junctions of these organs or around these organs and (b) securely attaching other gastro-intestinal implants that selectively restrict passage of food and organ secretions from one site within the gastro-intestinal tract to other sites within the gastro-intestinal tract, to these low-profile implants.

According to various embodiments, the present invention is a method for creating a reversible treatment for metabolic disorders such as diabetes and obesity and gastro-esophageal reflux disease (GERD) consisting of (a) placing low-profile implants that can be affixed within the stomach, the esophagus, the intestine or at internal junctions of these organs or around these organs and (b) placing other gastro-intestinal implants that selectively restrict passage of food and organ secretions from one site within the gastro-intestinal tract to other sites within the gastro-intestinal tract, to these low-profile implants and not to the tissue so that the procedure can be reversed easily.

According to various embodiments, the present invention is a modular gastrointestinal implant system for treating metabolic disorders such as diabetes and obesity by creating partial internal bypasses of food and organ secretions within the gastro-intestinal tract. The system includes an anchoring element configured for engaging an esophagus, the anchoring element having a docking feature; a first gastrointestinal implant having a coupling feature for engaging and coupling with the docking feature of the anchoring element and sized and shaped to extend from the esophagus to the duodenal bulb; wherein the docking feature and coupling feature are configured such that the first implant may releasably couple with the anchoring element to facilitate removal of the tubular implant; and a second gastrointestinal implant adapted to extend from the stomach or the duodenal bulb into the duodenum; wherein the first and second implants are adapted to partially overlap within the duodenal bulb.

According to some embodiments, the present invention is a modular gastrointestinal implant system for treating metabolic disorders such as diabetes and obesity by creating partial internal bypasses of food and organ secretions within the gastro-intestinal tract. The system includes a first anchoring element configured for engaging an esophagus, the first anchoring element having a docking feature; a second anchoring element configured for engaging a duodenum; a first gastrointestinal implant having a proximal end including a coupling feature for engaging the docking feature of the first anchoring element and a distal end adapted to couple with the second anchoring element; wherein the docking feature and coupling feature are configured such that the first implant may releasably couple with the anchoring element to facilitate removal of the tubular implant; and a second gastrointestinal implant adapted to extend from the stomach or the duodenal bulb into the duodenum, the second implant adapted to couple with the second anchoring element;

wherein the first and second implants are adapted to partially overlap within the second anchoring element.

According to various embodiments, the present invention is a method of treating metabolic conditions such as diabetes and obesity, which method includes securing a first anchoring element to the esophagus, the first anchoring element having a docking feature; securing a second anchoring element to the duodenum; implanting a first gastrointestinal implant having a proximal end including a coupling feature for engaging the docking feature of the first anchoring element and a distal portion adapted to couple with the second anchoring element; releasably coupling the coupling feature of the first gastrointestinal implant with the docking feature of the first anchoring element and coupling the distal portion with the second anchoring element; implanting a second gastrointestinal implant adapted to extend from the stomach or the duodenal bulb into the duodenum, the second implant adapted to couple with the second anchoring element; coupling the second implant to the second anchoring element, such that the first and second implants partially overlap within the second anchoring element.

According to various embodiments, the present invention is a gastrointestinal implant system for treating metabolic disorders such as diabetes and obesity by creating partial internal bypasses of food and organ secretions within the gastro-intestinal tract, which system includes a first gastrointestinal implant having a feature for engaging and coupling with the docking feature of the anchoring element and sized and shaped to extend from the esophagus to the duodenal bulb; and a second gastrointestinal implant adapted to extend from the stomach or the duodenal bulb into the duodenum; wherein the first and second implants are adapted to partially overlap within the duodenal bulb.

Furthermore, other documents that contemplate gastric and intestinal bypass using sleeve elements (e.g., WO/2007/136468) have a significant drawback. The sleeve element between the esophagus and the intestine passing through the stomach has no propulsion means to push food forward. Hence, if all the food from the esophagus (which is at this stage in semi-solid form) were to enter this section of the sleeve, it is possible there will be a backup of food causing dysphagia-like symptoms in the patient. Embodiments of the present invention describe partial bypass elements where only part of the food bypasses the stomach, such that if there is resistance to the passage of the food through the sleeve element, the food has an alternative pathway to move forward hence eliminating the chances of dysphagia.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
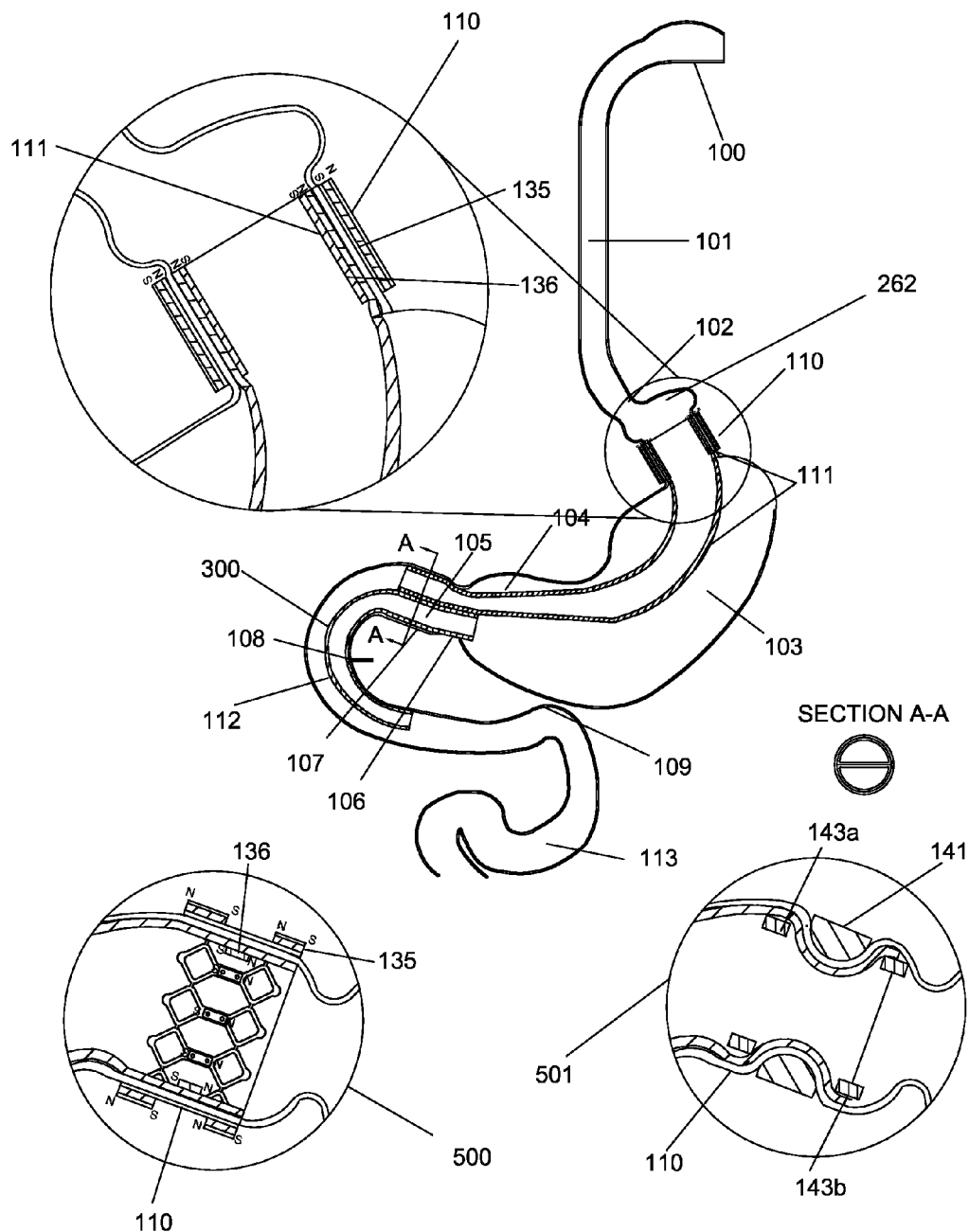
FIGS. 1-4 are sectional views of a portion of the digestive tract in the body showing partial bypass systems having an external band implanted around the outside diameter of the esophagus and a first tubular implant (sleeve) implanted inside the esophagus and anchored to the external band. A first tubular implant extends through the stomach into the duodenal bulb and a second implant (sleeve) is implanted in the stomach antrum and extends into and/or through the duodenum.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
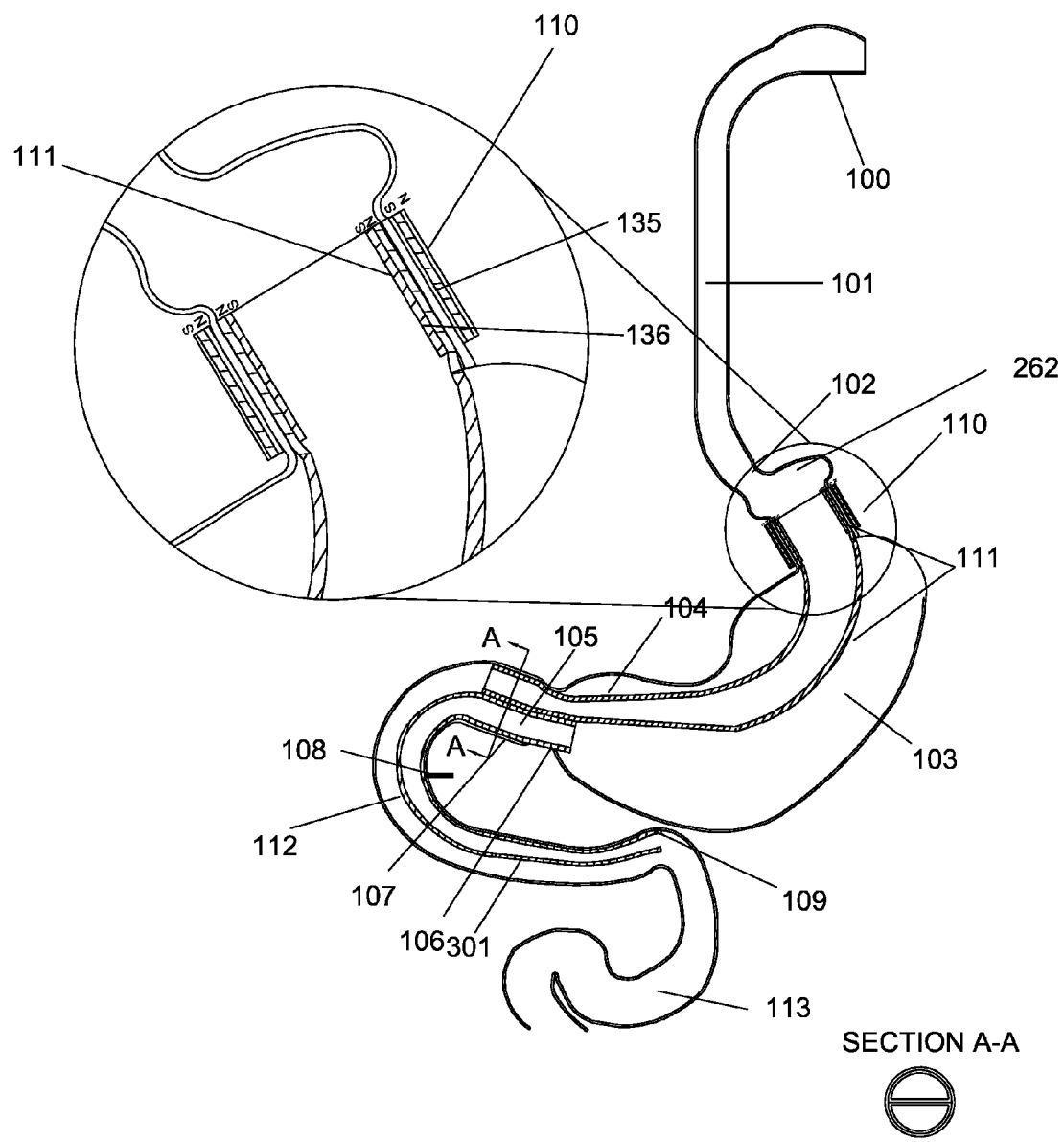

FIGS. 1 and 2 are sectional views of a portion of the digestive tract in a human body. As a person ingests food, the food enters the mouth 100, is chewed, and then proceeds down the esophagus 101 to the lower esophageal sphincter at the gastro-esophageal junction 102 and into the stomach 103. The food mixes with enzymes in the mouth 100 and in the stomach 103. The stomach 103 converts the food to a semi-fluid substance called chyme. The chyme enters the pyloric antrum 104 and exits the stomach 103 through the pylorus 106 and pyloric orifice 105. The small intestine is about 21 feet long in adults and is comprised of three sections: the duodenum 112, the jejunum 113, and the ileum (not shown). The duodenum 112 is the first portion of the small intestine and is typically 10-12 inches long. The duodenum 112 is comprised of four sections: the superior, descending, horizontal and ascending sections. The duodenum 112 ends at the ligament of Treitz 109. The papilla of Vater 108 is the duct that delivers bile and pancreatic enzymes to the duodenum 112. The duodenal bulb 107 is the portion of the duodenum which is closest to the stomach 103.

As shown, an external anchoring element or band 110 is secured or positioned around the outside of the esophagus and a first gastrointestinal or tubular implant 111 (e.g., sleeve) is implanted inside of the esophagus and anchored magnetically through the esophageal tissue to the external band 110. As shown in FIG. 1, magnets 135 on the anchoring element 110 and magnets 136 on the tubular implant 111 magnetically interact with (e.g., attraction, repulsion, or levitation) each other to anchor or secure the tubular implant 111 to the external band 110 in a removable or reversible configuration. The magnets 135 on the external anchoring element or band 110, which can be located on the inside surface, outside surface, or embedded in the middle of the band, serve as a coupling or docking feature. The magnets 136 on the tubular implant 111, which magnetically interact with the magnets 135 on the anchoring element, serve as a coupling feature for the implant 111. Suitable exemplary materials for the magnets include neodymium-iron-boron [Nd—Fe—B], samarium-cobalt [Sm—Co], alnico, and hard ferrite [ceramic]. The magnets may be plated with gold or platinum or other material to make them radio-opaque or to improve the corrosion resistance. The magnets may be encapsulated within a metal casing such as titanium or stainless steel to improve the corrosion resistance and the biocompatibility. According to various embodiments, the external band 110 is made from one or more elastomers (e.g., silicon, polyurethane, and ePTFE), metals, or fabrics (e.g., Dacron or a combination of polymers and textile materials).

As shown, the gastrointestinal implant 111 extends into the duodenum 112 to the duodenal bulb 107. According to some embodiments, the sleeve 111 or the anchor mechanism 110 may form a restrictive stoma 262 in the esophagus (see FIGS. 1 and 2), for example, by reducing or restricting the internal diameter of the esophagus. According to other embodiments, as shown for example in FIGS. 3 and 4, a stoma is not formed. A second sleeve 300 or 301 is implanted from the stomach antrum 104 (or from the duodenal bulb 107) to the midportion of the duodenum (see, e.g. FIG. 1) or to the ligament of Treitz (see, e.g., FIG. 2). According to some embodiments, the two sleeves each form a D-shaped transverse section in the overlap section (e.g., the region in or near the duodenal bulb 107), such that when combined they together form a generally circular overall transverse cross-section (see, e.g., section A-A in FIGS. 1 and 2). The first sleeve 111 (extending between the esophagus 102 and the duodenal bulb 107) serves to bypass the stomach 103. The second sleeve 300 (or sleeve 301) allows the stomach secretions to bypass a portion (or all) of the duodenum 112. According to some embodiments, at least one of the first sleeve 111 and the second sleeve 300 are formed or shaped such that the portion of the sleeve located in the duodenal bulb has and generally holds the D-shape cross section (as shown in section A-A). In other embodiments, these portions of the first sleeve and/or second sleeve 300 are not preformed or shaped, but instead are made from a material having sufficient compliance to conform to the duodenal bulb, in such a way as to have a substantially D-shape cross section.

According to other embodiments, the anchoring mechanism 110 may be formed from other structures. Exemplary structures (shown in FIG. 1) include a stent 500 and/or interlocking mechanical rings 501. The stent 500 can be a self expanding type or a balloon expandable type. As shown, the rings 501 are configured such that an outer ring 141 positioned around an outer surface of the esophagus is sized and shaped to interlock with an inner ring 143a or 143b positioned around an inner surface of the esophagus. According to some embodiments, the anchoring mechanism 110 is integrally formed with the sleeve 111, and, in other embodiments, the anchoring mechanism is structurally separate from and adapted for coupling with the sleeve 111. According to other embodiments, any of the internal anchoring structures disclosed in co-pending, commonly assigned U.S. patent application Ser. No. 12/752,697 (incorporated herein by reference) may be used as the anchoring mechanism 110. According to still other embodiments, any of the external anchoring structures disclosed in co-pending, commonly assigned U.S. patent application Ser. No. 12/833,605 (incorporated herein by reference) may be used as the anchoring mechanism 110. Likewise, the implants or sleeves 111 and 300 may be formed in any configuration or from any material disclosed in either of U.S. patent application Ser. Nos. 12/752,697 or 12/833, 605. Likewise the implants or sleeves may be couples or anchored to the anchoring mechanism using any arrangement disclosed in either of U.S. patent application Ser. Nos. 12/752,697 or 12/833,605.

Figure 3:
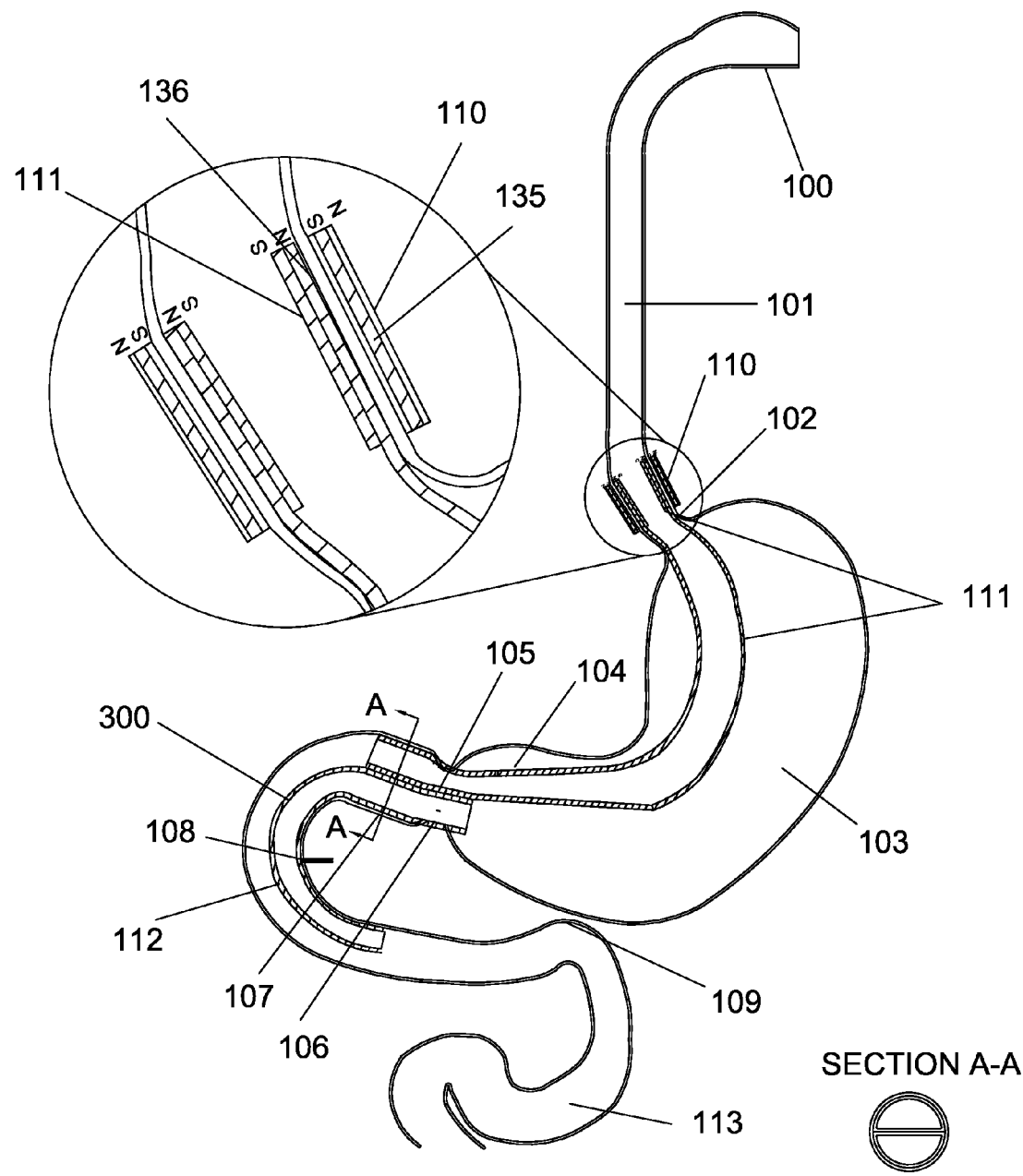
Figure 4:
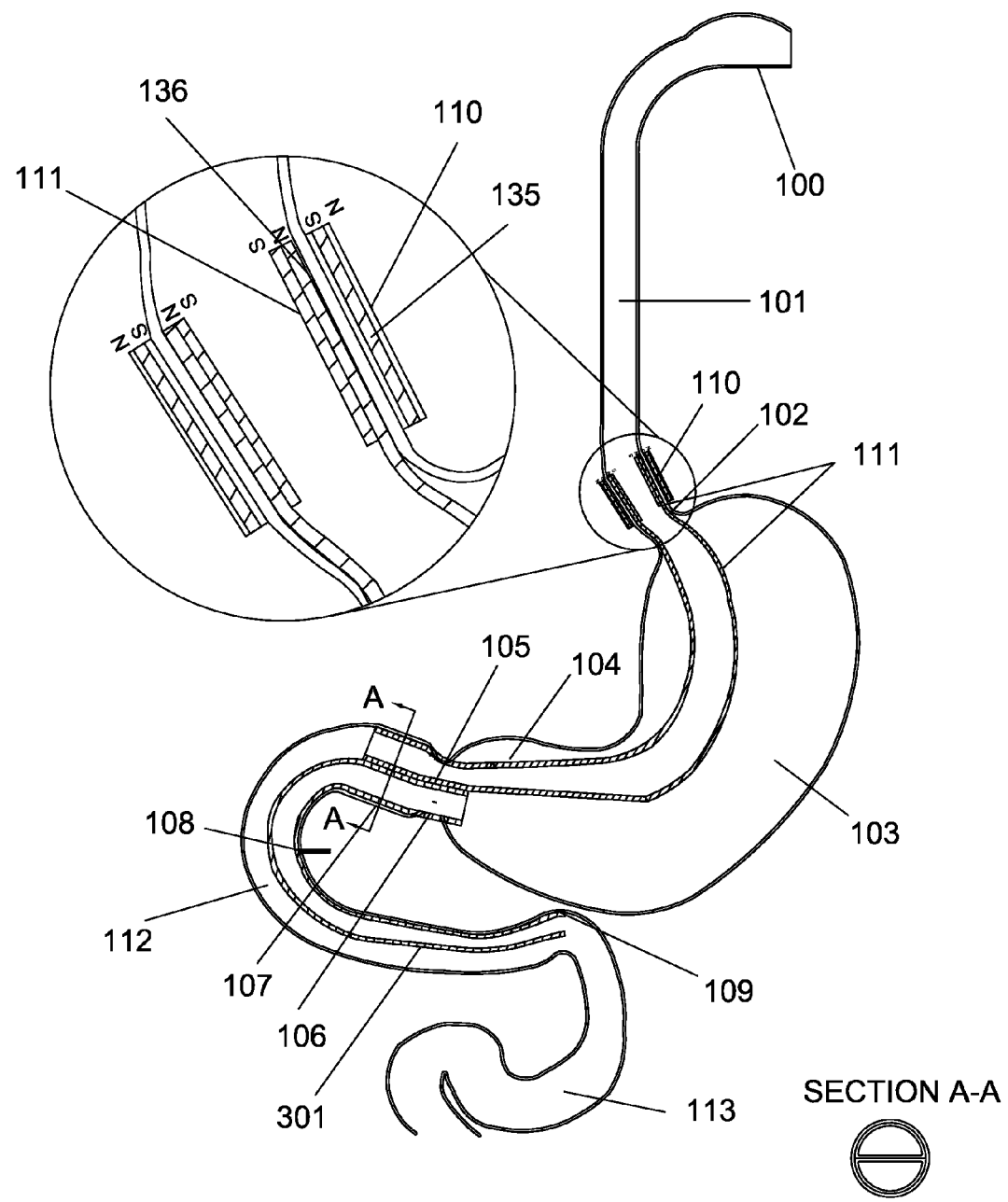

FIG. 3 is an alternative embodiment of FIG. 1 where the tubular implant does not cause or form a stoma in the esophagus. FIG. 4 is an alternative embodiment of FIG. 2 where the tubular implant does not cause or form a stoma in the esophagus.

Figure 5:
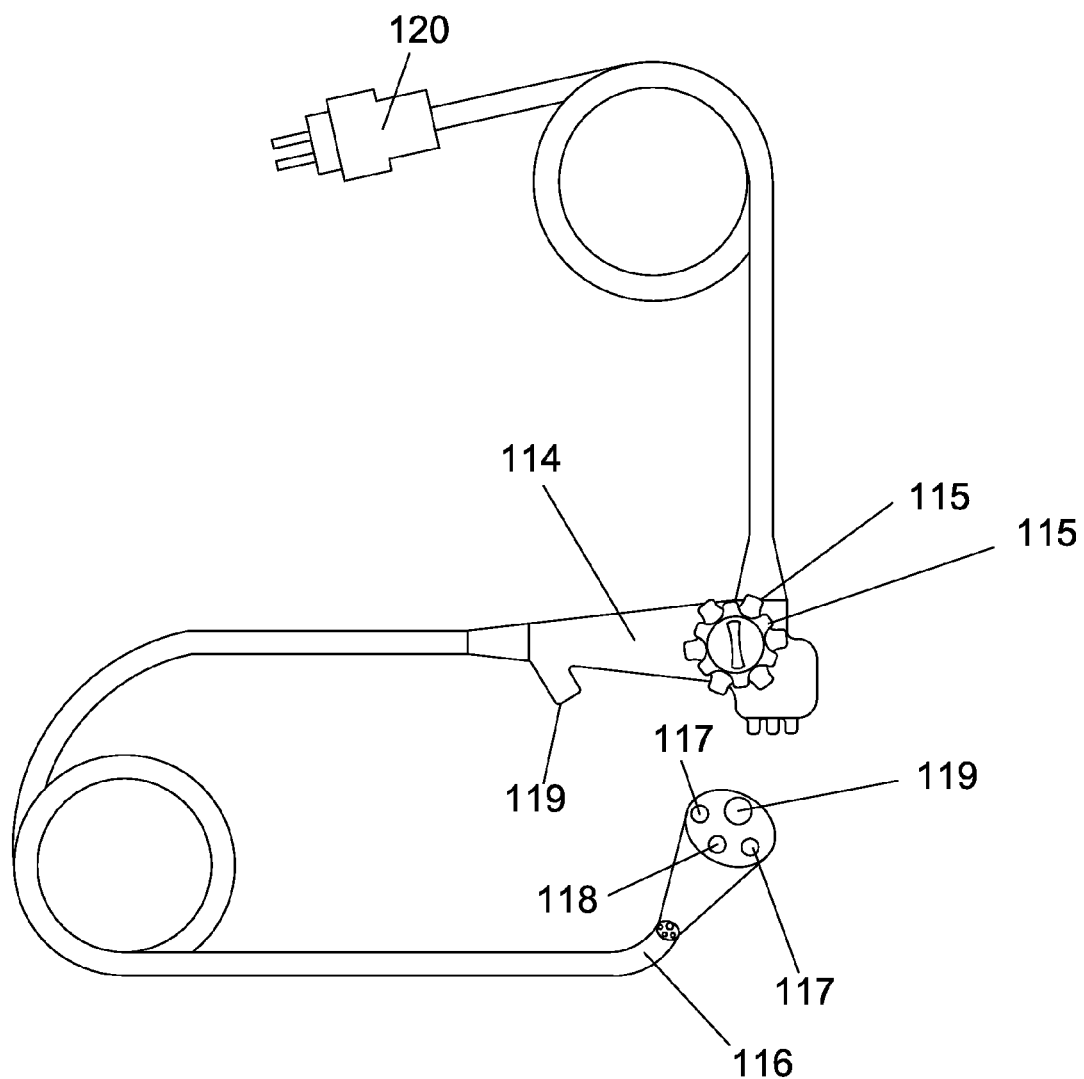
FIG. 5 shows an exemplary endoscope used for diagnostic and therapeutic procedures in the gastro intestinal (GI) tract.

FIG. 5 shows an endoscope 114. Endoscopes 114 are used for diagnostic and therapeutic procedures in the gastrointestinal (GI) tract. The typical endoscope 114 is steerable by turning two rotary dials 115 to cause deflection of the working end 116 of the endoscope. The working end (or distal end) of the endoscope 116 typically contains two fiber bundles for lighting 117, a fiber bundle for imaging 118 (viewing) and a working channel 119. The working channel 119 can also be accessed on the proximal end of the endoscope. The light fiber bundles and the image fiber bundles are plugged into a console at the plug in connector 120. The typical endoscope has a working channel in the 2.6 mm to 3.2 mm diameter range. The outside diameters of the endoscopes are typically in the 8 mm to 12 mm diameter range, depending on whether the endoscope is for diagnostic or therapeutic purposes.

Figure 6:
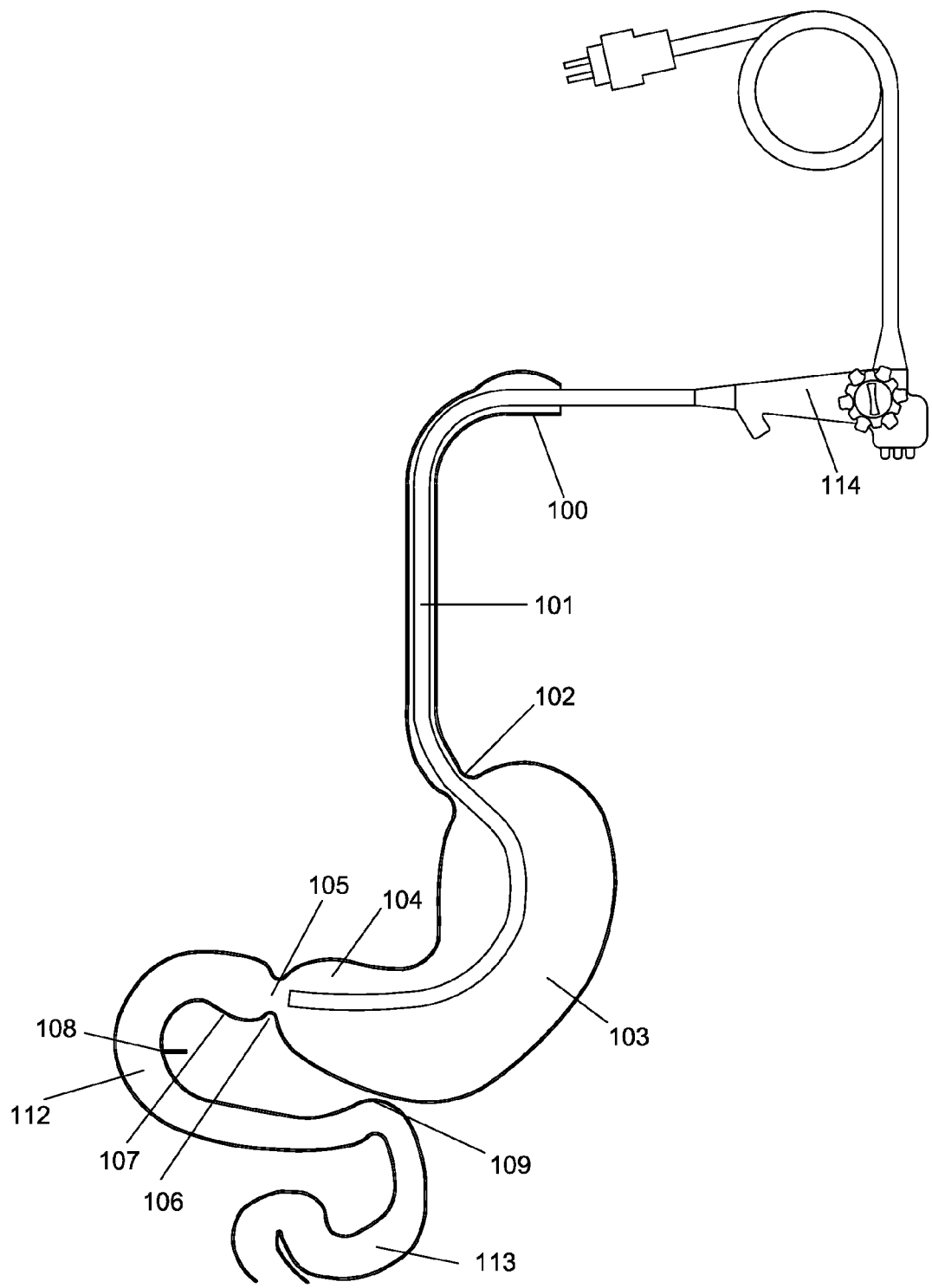
FIG. 6 is a sectional view of a portion of the digestive tract in the body, with an endoscope passing through the esophagus into the stomach, and the end of the scope positioned to allow viewing of the pylorus.

FIG. 6 shows a sectional view of a portion of the digestive tract in a human body. As shown in FIG. 6, an endoscope 114 has been inserted through: the mouth 100, esophagus 101, stomach 103 and pyloric antrum to allow visualization of the pylorus 106.

Figure 7:
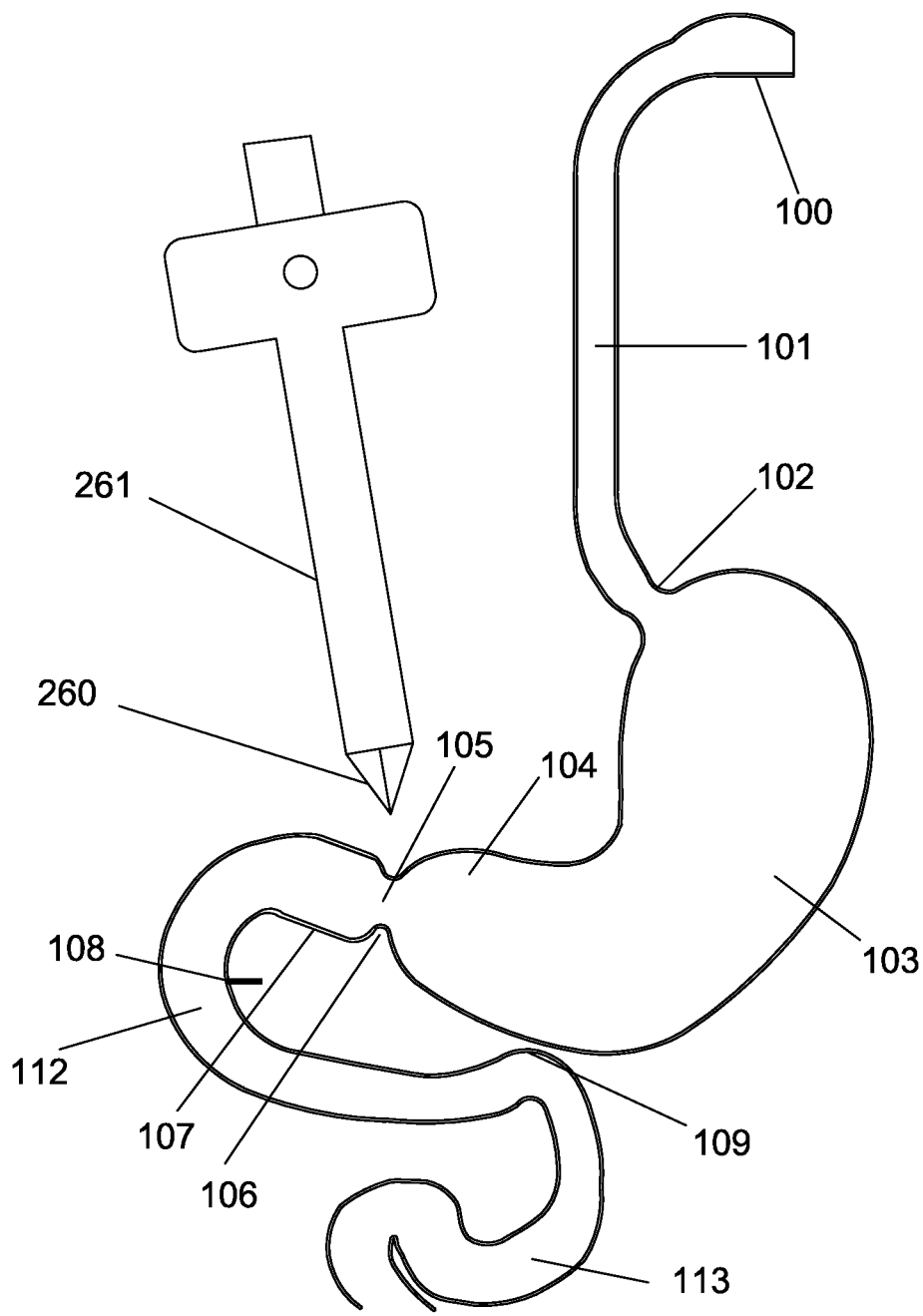
FIG. 7 is a schematic view showing a trocar and cannula operable to access the implant location of the duodenal bulb using laparoscopic techniques.

FIG. 7 shows a sectional view of a portion of the digestive tract in the body with a trocar 260 and cannula 261 inserted to access the implant location of the duodenal bulb, gastroesophageal junction, or other suitable location using laparoscopic techniques. An alternative access route is to use natural orifice surgery (e.g., access via the esophagus, stomach, belly button or vagina).

Figure 8:
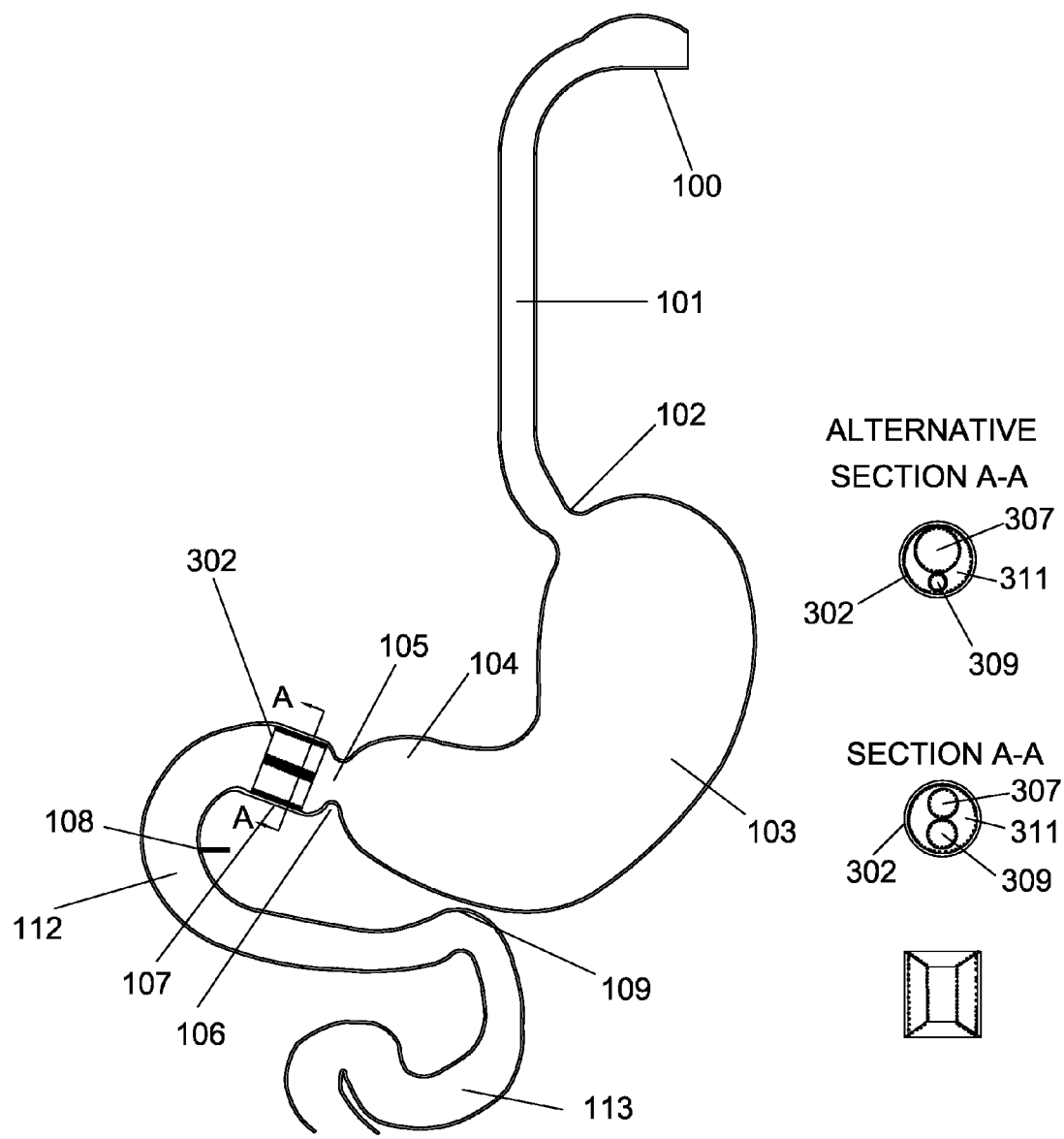
FIG. 8 is a sectional view of a portion of the digestive tract in the body. An implant is implanted in the duodenal bulb. The implant has two interior lumens as in section A-A or the alternative section A-A that allow two tubular implants to be sleeved adjacent to each other (i.e., overlapping).

FIG. 8 shows a sectional view of a portion of the digestive tract in the body. As shown, a bifurcated anchor or implant 302 is implanted in the duodenal bulb 107 or pylorus 106. The implant has two interior lumens or anchoring structures 307, 309, as shown in section A-A or the alternative section A-A, that may couple with or otherwise allow two tubular implants to be sleeved adjacent to each other (i.e., overlapping). According to other embodiments, the implant 302 is structured to have D-shaped transverse sections, as shown above for example in section A-A in FIGS. 1 and 2. According to various embodiments, the implant 302 is configured to couple or anchor to the duodenal bulb 107 (or pylorus 106) and serves as an anchoring location for an end of the tubular implants or sleeves. According to various embodiments, the anchoring mechanism 110 includes structures to urge or otherwise cause the overlapping portions of the first sleeve 111 and the second sleeve 300 to form a specified shape, such as the D-shape described above and shown, for example, in section A-A of FIG. 1.

In the embodiments such as that shown in section A-A, the implant 302 further includes an area 311 which is located inside the implant 302 and outside the lumens 307, 309. The anchor or implant 302, according to various embodiments, includes a transition or seal feature covering the area 311 (shown for example in FIG. 8 below section A-A). This transition of seal feature may be shaped and configured to block or cover the area 311 (either partially or entirely), such that materials exiting the stomach cannot substantially bypass the sleeves coupled to either of the lumens 307, 309. In various embodiments, this seal feature may be a sleeve, film or other structure made from, for example, a urethane or Goretex material. In some embodiments, the area 311 is covered with a structure made from one or more elastomers (e.g., silicon, polyurethane, and ePTFE), metals, or fabrics (e.g., Dacron or a combination of polymers and textile materials).

Figure 9:
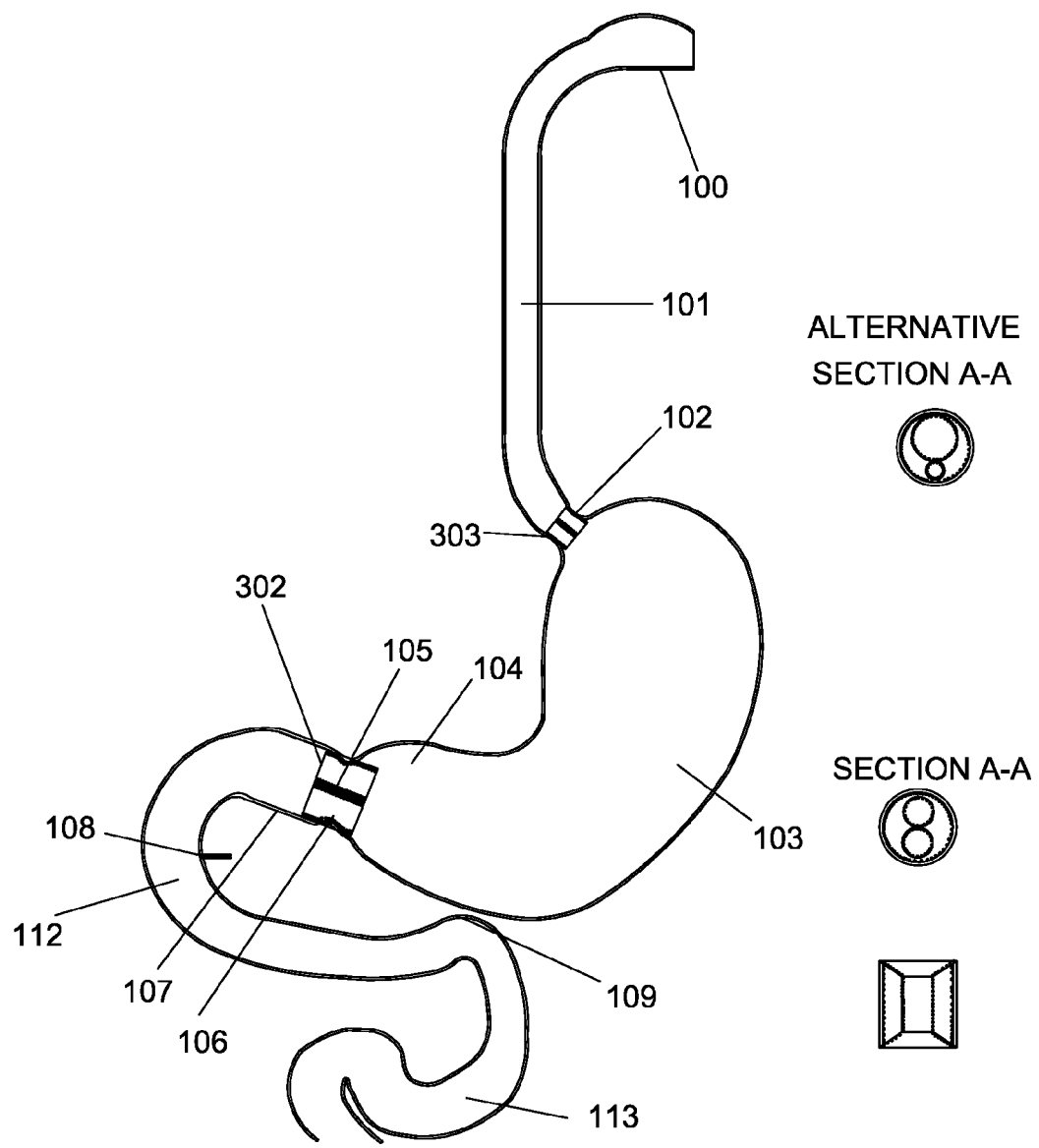
FIG. 9 is a sectional view of a portion of the digestive tract in the body. A first implant is implanted in the duodenal bulb and a second implant is implanted in the esophagus. The implants have two interior lumens as in section A-A or the alternative section A-A that allow two tubular implants to be sleeved adjacent to each other (i.e., overlapping).

FIG. 9 shows a sectional view of a portion of the digestive tract in the body. As shown, a bifurcated implant 302 is implanted into the duodenal bulb 107 (or pylorus 106). A second bifurcation implant 303 is implanted in the esophagus 102. According to various embodiments, the second implant 303 is formed of any of the configurations described above with respect to the bifurcated implant 302.

Figure 10:
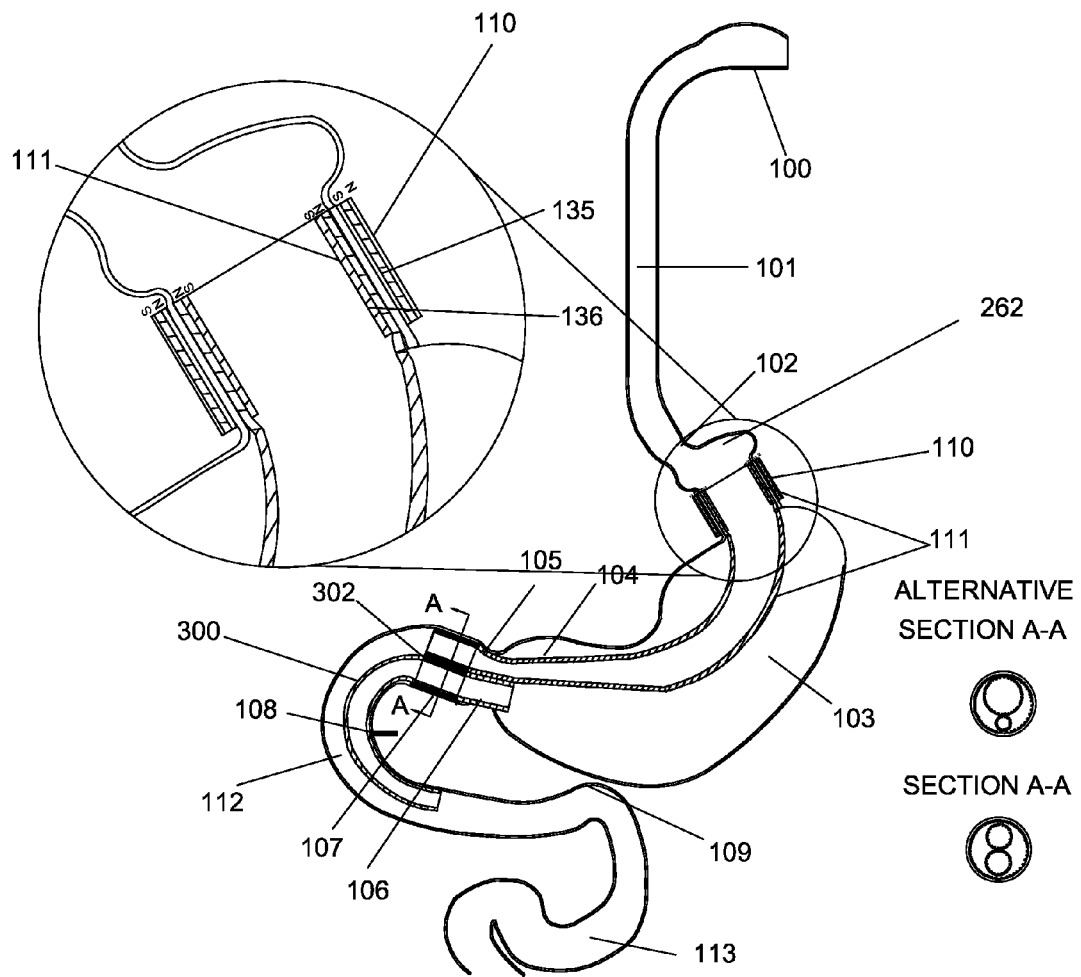
FIGS. 10 and 11 are sectional views of a portion of the digestive tract in the body. An external anchor is positioned around the outside diameter of the esophagus and a bifurcation implant is implanted into the duodenal bulb. A first tubular implant (sleeve) is implanted in the esophagus and is anchored to the external anchor at a proximal portion and to the implant at a distal portion. A second sleeve is implanted in the stomach antrum extending into and/or through the duodenum.

FIG. 10 is a sectional view of a portion of the digestive tract in a human body. As shown, a tubular implant 111 (sleeve) is implanted inside the esophagus (e.g., on the inside surface) and anchored mechanically or magnetically (as further described above) through the esophageal tissue to the external band 110 which is secured around the outside of the esophagus. As shown, the tubular implant 111 extends into the duodenum 112 to the duodenal bulb 107. The sleeve in the esophagus may form a restrictive stoma 262 in the esophagus. A second sleeve 300 is implanted from the stomach antrum 104 to the mid-portion of the duodenum.

Figure 11:
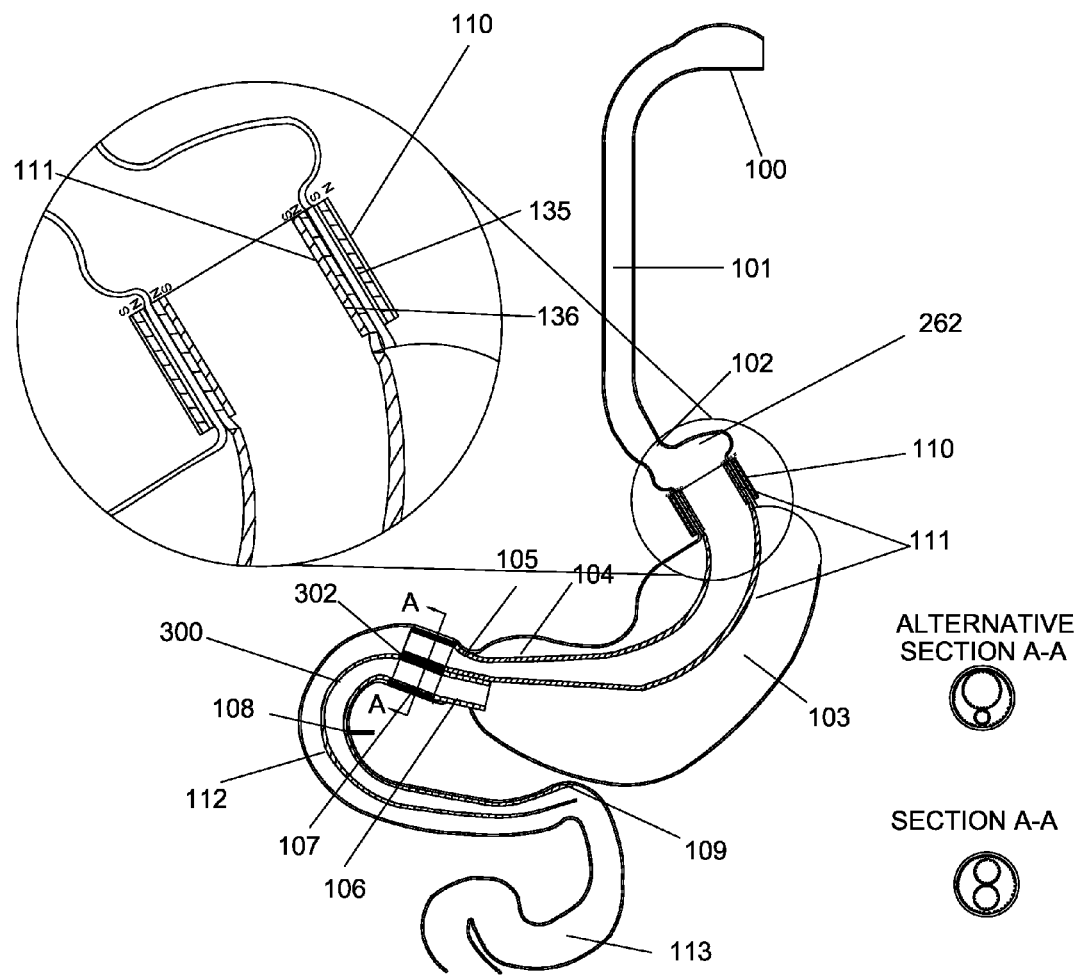

As further shown in FIGS. 10 and 11, the two sleeves are inserted into a bifurcated implant 302 to anchor the sleeves and form the transition shape. According to some embodiments, the two sleeves each form a circular shape individually in the overlapping section. The two round sections of the implant form a combined round outer diameter (see, e.g., section A-A in FIG. 10). According to other embodiments, the overlapping ends of the sleeves 111, 300 (i.e., the distal end of the sleeve 111 and the proximal end of the sleeve 300) are formed with (or are otherwise capable of conforming to) a D-shaped section, such that collectively the ends form a generally circular transverse section shape. The sleeve between the esophagus 102 and the duodenal bulb 107 bypasses the stomach 103. The second sleeve is located from the distal stomach antrum 104 (or pylorus) to the mid-duodenum (see FIG. 10) or to the ligament of Treitz (see FIG. 11). The second sleeve 300 allows stomach secretions to bypass a portion of the duodenum 112.

Figure 12:
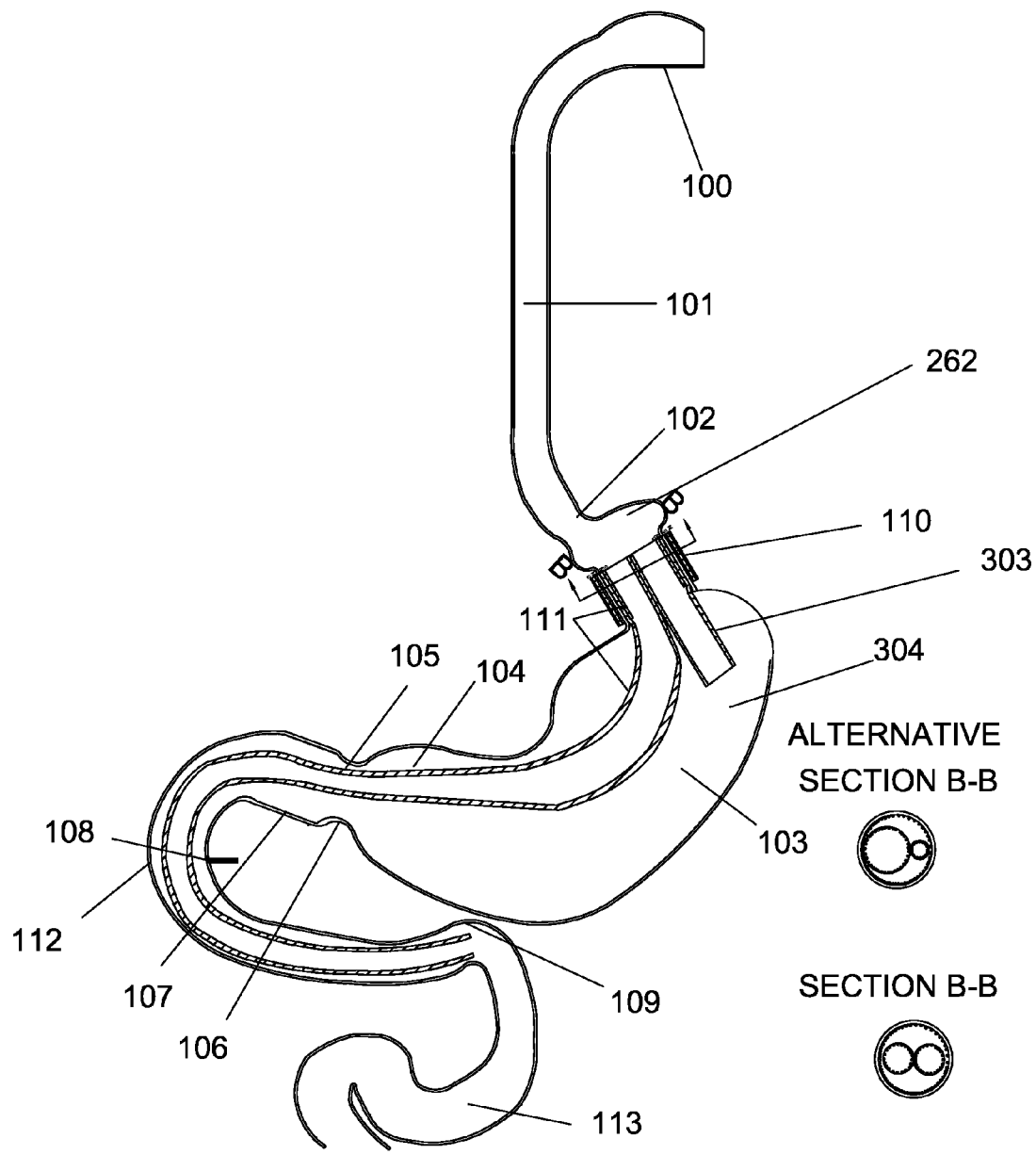
FIGS. 12 and 13 are sectional views of a portion of the digestive tract in the body. An external anchor is positioned around the outside of the esophagus and a first tubular implant (sleeve) is implanted in the esophagus and anchored to the external anchor. The first tubular implant extends through the duodenum to the ligament of Treitz. A second sleeve is anchored to the external anchor and extends into and/or through the stomach.
Figure 13:
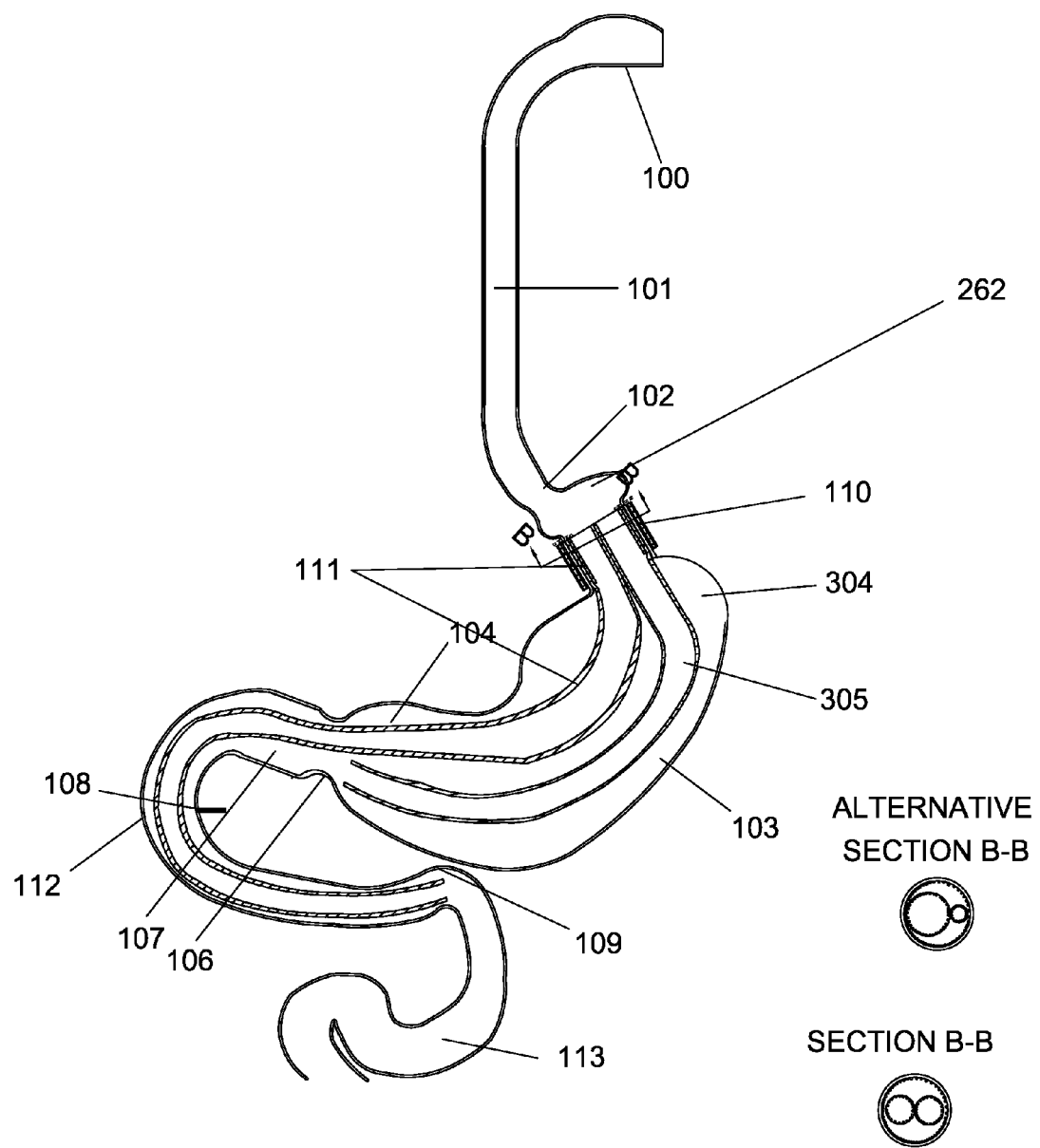

FIGS. 12 and 13 show sectional views of a portion of the digestive tract in the body. As shown, an external band 110 is implanted around the outside of the esophagus. According to other embodiments, a bifurcated implant is implanted inside the esophagus. A tubular implant 111 (sleeve) is implanted on the inside surface of the esophagus and anchored magnetically or mechanically through the esophageal tissue to the external band 110. The tubular implant 111 extends into the duodenum (e.g., to the ligament of Treitz). As shown, the anchor or band around the esophagus forms a restrictive stoma 262 in the esophagus. A second sleeve 303 is implanted from the esophagus (again, anchored to the external band 110 or bifurcated implant) and extends into the upper portion of the stomach near the fundus 304 (see FIG. 12) or the lower portion of the stomach near the antrum 104 (see FIG. 13).

Figure 14:
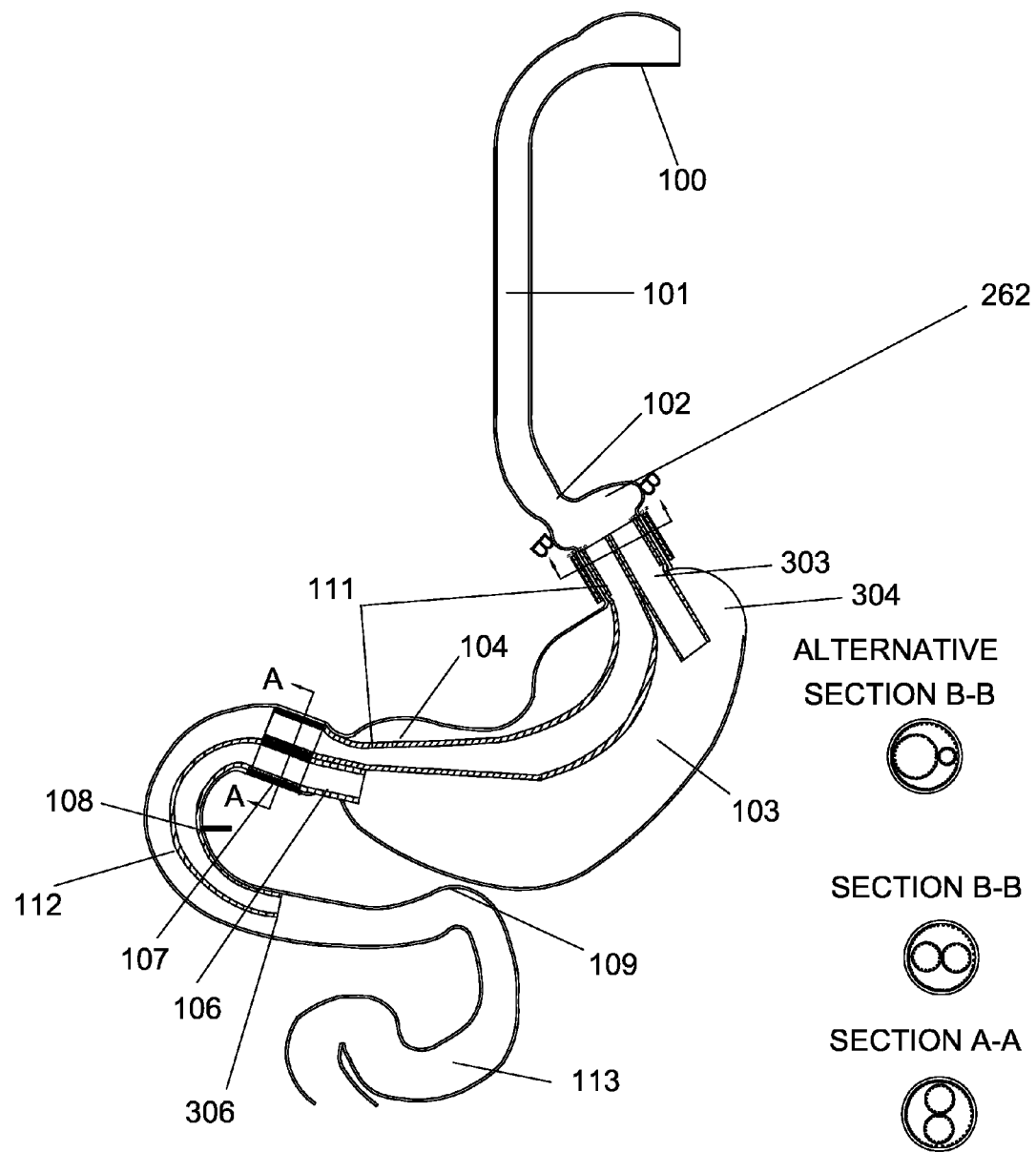
FIGS. 14-16 are sectional views of a portion of the digestive tract in the body. An external anchor is implanted around the outside of the esophagus and a first tubular implant (sleeve) is implanted in the esophagus and anchored to the external anchor. The first tubular implant extends into the duodenum to duodenal bulb. A second sleeve is implanted from the esophagus into the stomach. A third sleeve is implanted from the pylorus or stomach antrum into or through the duodenum.
Figure 15:
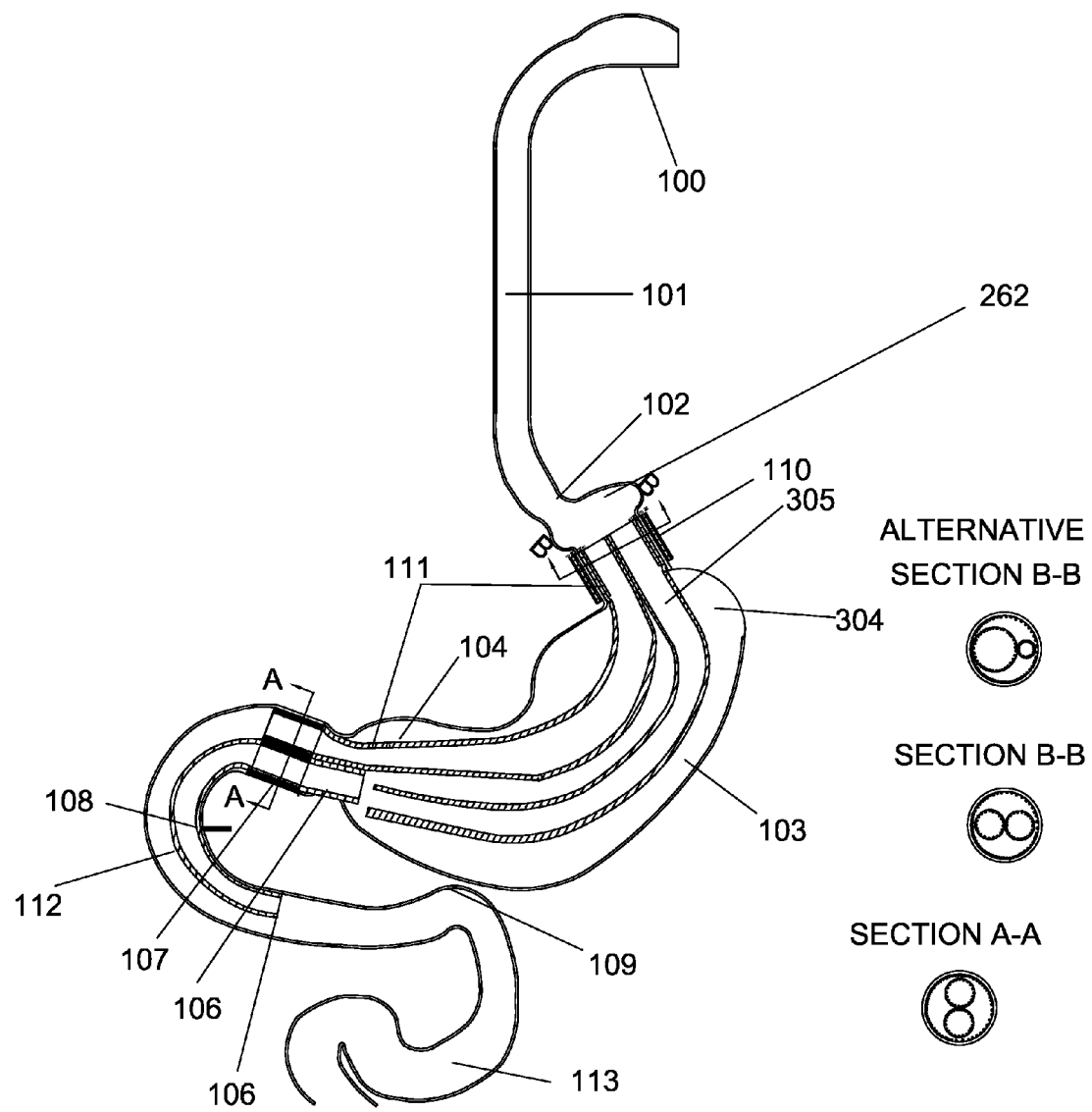
Figure 16:
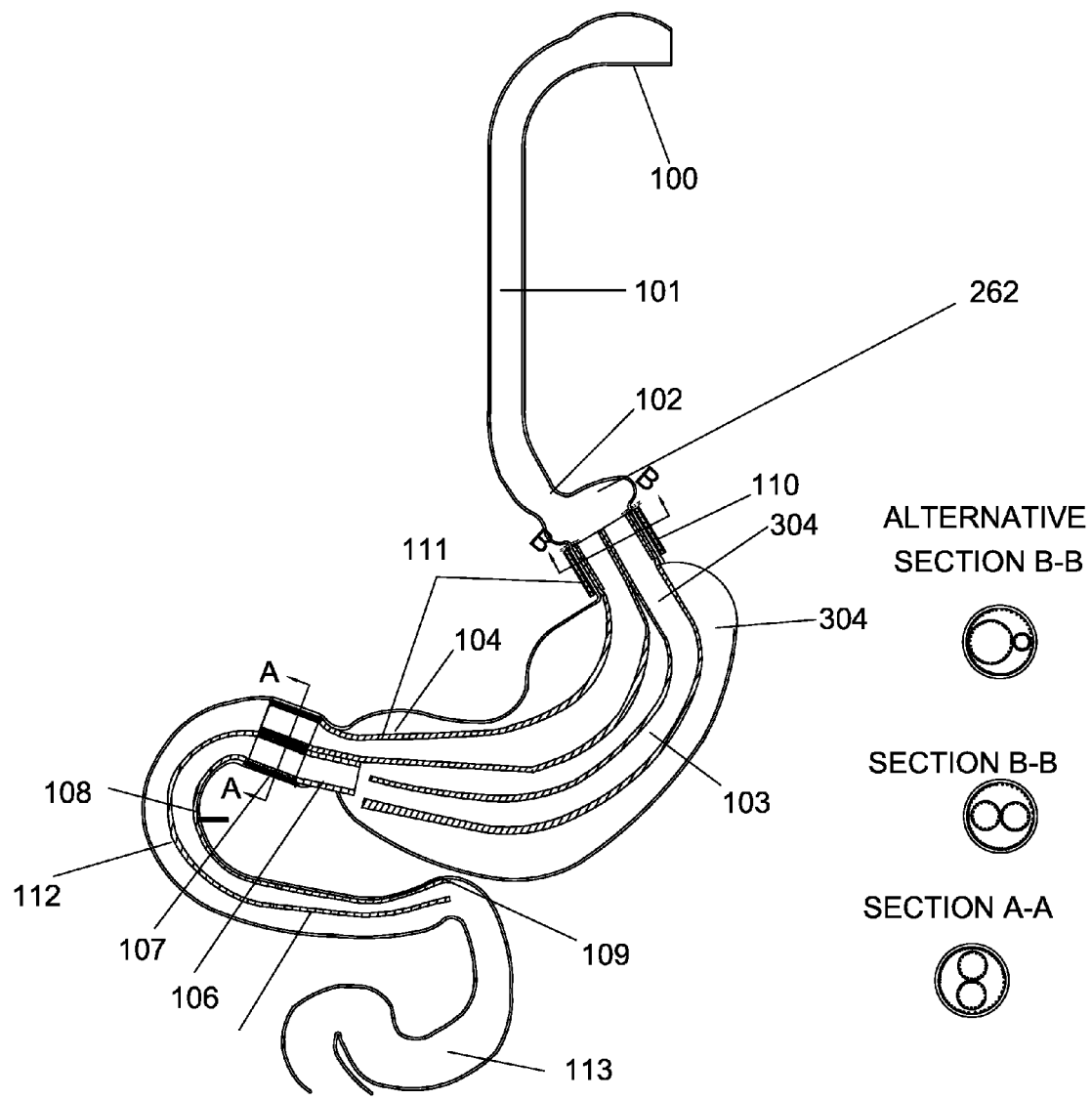

The two sleeves can each form a circular shape individually (see, e.g., section B-B and alternative section B-B) in the overlap section in the esophagus or alternatively the overlap portions of the sleeves can have or otherwise form D-shaped sections. The tubular element or sleeve 111 of the bypass system delivers food and secretions past the upper duodenum where as the rest of the food is allowed to flow into the upper duodenum where it will mix with the biliopancreatic secretions thus creating a partial duodenal bypass where controlled gastric emptying is still functional. Because of some level of biliopancreatic interaction with the food, this type of procedure is likely to result in the patient experiencing less complications such protein deficiency FIGS. 14-16 show sectional views of a portion of the digestive tract in the body. As shown, an external anchor or band 110 is implanted around the outside diameter of the esophagus (or alternatively a bifurcated implant is implanted inside). A tubular implant 111 (sleeve) is implanted on the inside surface of the esophagus and anchored magnetically or mechanically through the esophageal tissue to the external band 110. The tubular implant 111 extends from the esophagus into the duodenal bulb where a distal portion of the implant 111 couples to bifurcated implant 302.

As shown, the anchor or band around the esophagus forms a restrictive stoma 262 in the esophagus. A second sleeve 303 is implanted from the esophagus (again, anchored to the external band 110 or bifurcated implant) and extends into the upper portion of the stomach near the fundus 304 (see FIG. 14) or the lower portion of the stomach near the antrum 104 (see FIGS. 15 and 16). As further described above, the two sleeves can each form a circular sectional shape (see section B-B in FIG. 14) in the overlap section in the esophagus or alternatively have or otherwise form D-shaped sections. A third sleeve 306 is implanted from the pylorus or stomach antrum and extends into the mid-duodenum (see, e.g., FIGS. 14 and 15) or to the ligament of Treitz (see, e.g., FIG. 16). The two sleeves overlapping in or near the duodenum (e.g., sleeve 111 and sleeve 306) can each form a circular shape (or alternatively D-shaped sections) as shown.

According to various embodiments, the gastrointestinal system includes two stents, a first stent in the esophagus and a second stent at the pyloric junction. The first stent couples to and secures a proximal portion of the implant 111 and a proximal portion of the second sleeve 303. The second stent couples to and secures a distal portion of the implant 111 and a proximal portion of the third sleeve 306.

As shown, the sleeve 111 includes a tubular element that bypasses a majority of the food ingested past the stomach emptying it in to the small intestine. The remainder of the food empties in to the stomach where it gets mixed with stomach enzymes and peptides such as Ghrelin released by the fundus of the stomach. The sleeve 306 at the pyloric junction redirects this mixture past the small intestine by means of the tubular element attached to it. Thus this system can mimic both the restrictive and malabsorptive features of a stomach reduction procedure as well as reduction of exposure of peptides such as Ghrelin to the upper duodenum.

An external anchor is positioned around the outside of the esophagus. A first tubular implant (sleeve) is implanted inside the esophagus and anchored to the external anchor and extends from the esophagus into the duodenum to the duodenal bulb. The first tubular implant has a valve (section C-C) opening that (like stoma) allows some portion of the food entering the esophagus to enter the upper portion of the stomach. A second sleeve is implanted from the stomach antrum into or through the duodenum.

Figure 17:
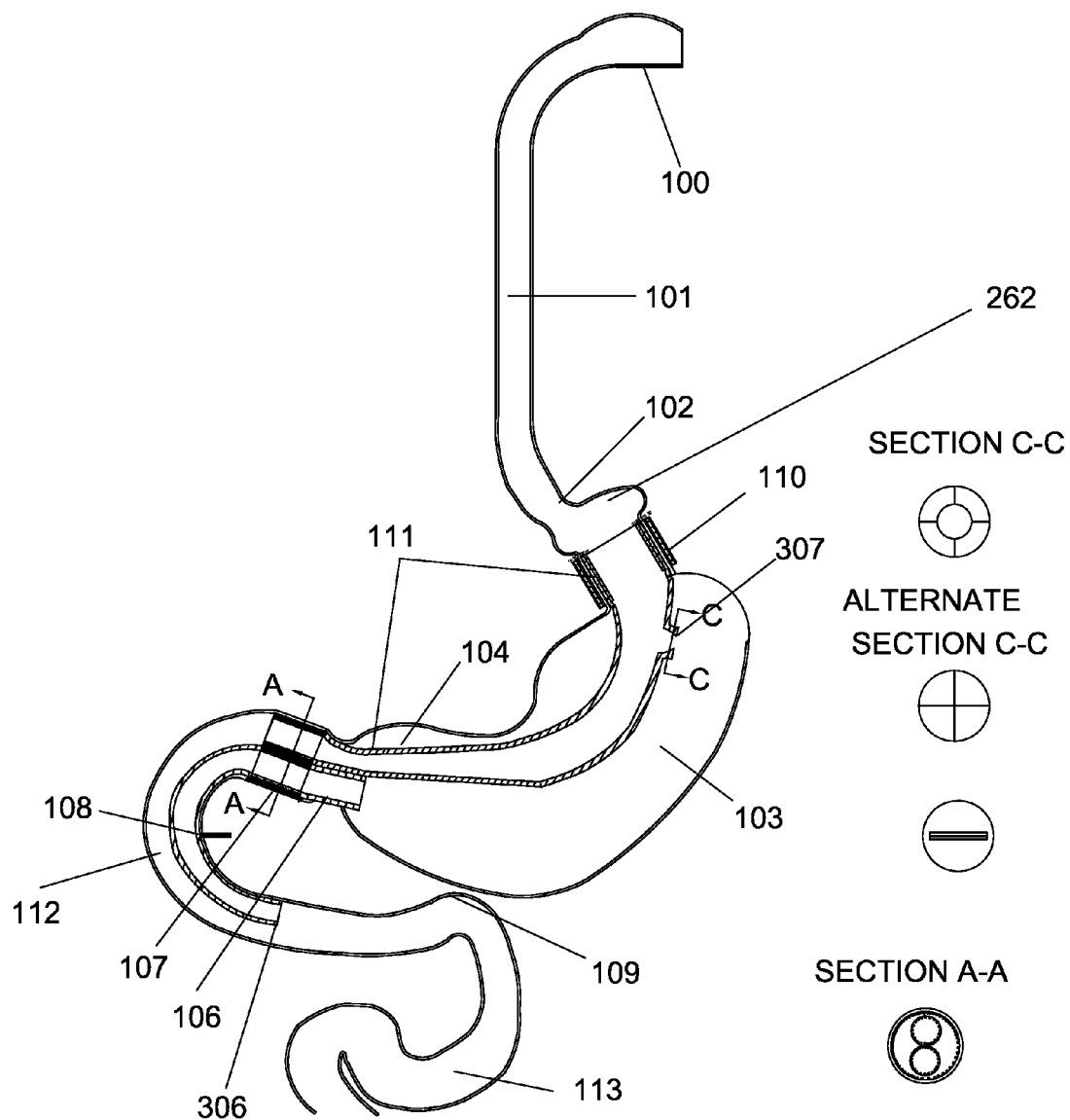
FIGS. 17-18 are sectional views of a portion of the digestive tract in the body. An external anchor is positioned around the outside of the esophagus. A first tubular implant (sleeve) is implanted inside the esophagus and anchored to the external anchor and extends from the esophagus into the duodenum to the duodenal bulb. The first tubular implant has a valve (section C-C) opening that (like stoma) allows some portion of the food entering the esophagus to enter the upper portion of the stomach. A second sleeve is implanted from the stomach antrum into or through the duodenum.
Figure 18:
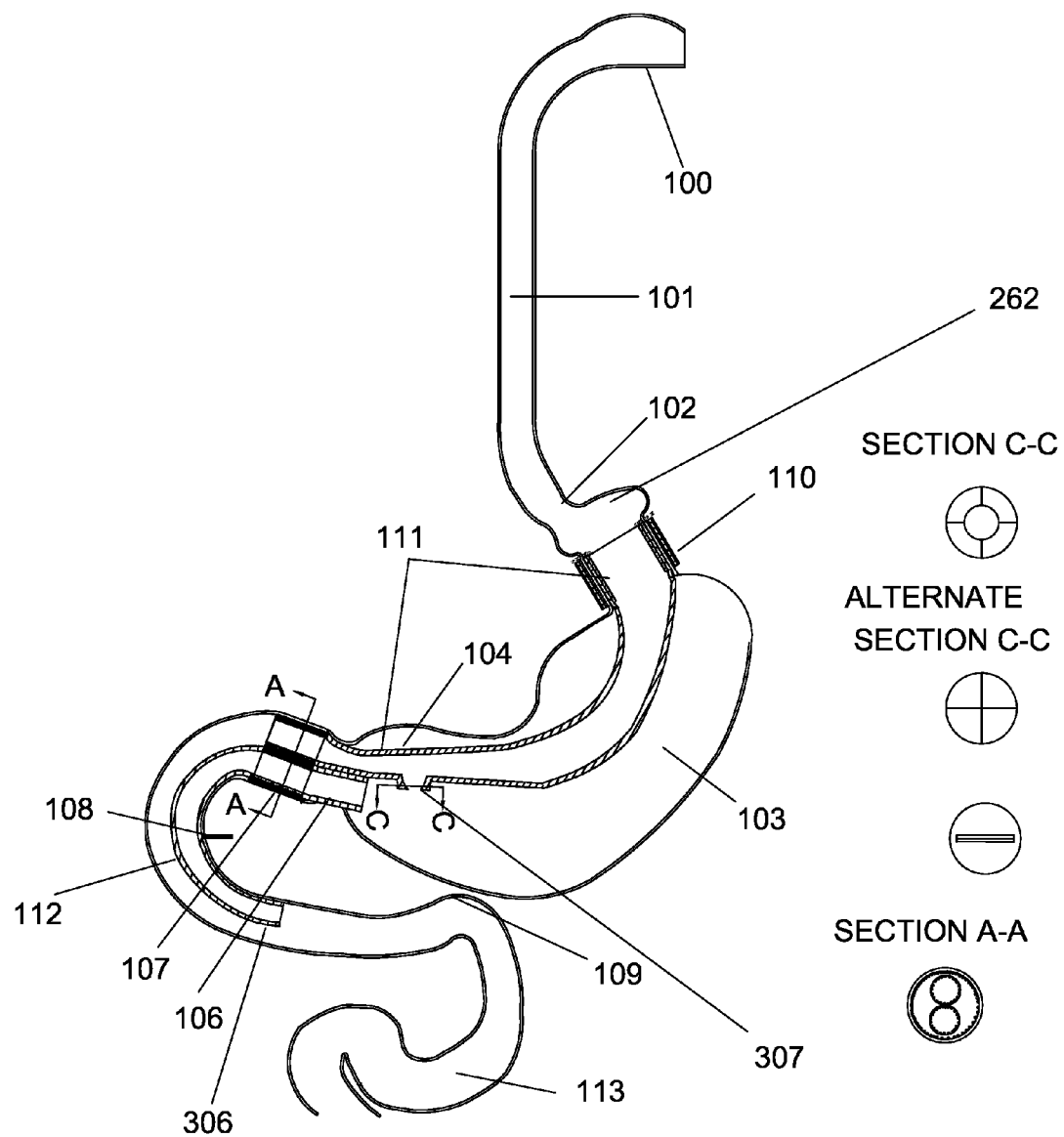

FIGS. 17 and 18 show sectional views of a portion of the digestive tract in the body. As shown, an external anchor or band is implanted around the outside of the esophagus. According to alternative embodiments, a bifurcated implant is implanted inside. A tubular implant 111 (sleeve) is implanted on the inside surface of the esophagus and anchored magnetically or mechanically through the esophageal tissue to the external band 110. The tubular implant 111 extends into the duodenum to the duodenal bulb. The band around the esophagus forms a restrictive stoma 262 in the esophagus. A valve 307 is constructed into the wall of the sleeve 111. The valve acts as a stoma that can allow a portion of the food entering the sleeve 111 to exit the stoma opening into stomach. According to various embodiments, the valve 307 is any of an opening, a hole, a slit, or a mechanical valve mechanism. Exemplary structures for the valve 307 are shown in section C-C and alternative sections C-C in FIGS. 17 and 18. A second sleeve 306 is implanted from the pylorus or stomach antrum to the midpoint of the duodenum. As further described above, the two sleeves can each form a circular shape individually in the overlap section in the esophagus or alternatively "D" shaped sections (see, e.g., section A-A in FIGS. 17 and 18).

Figure 19:
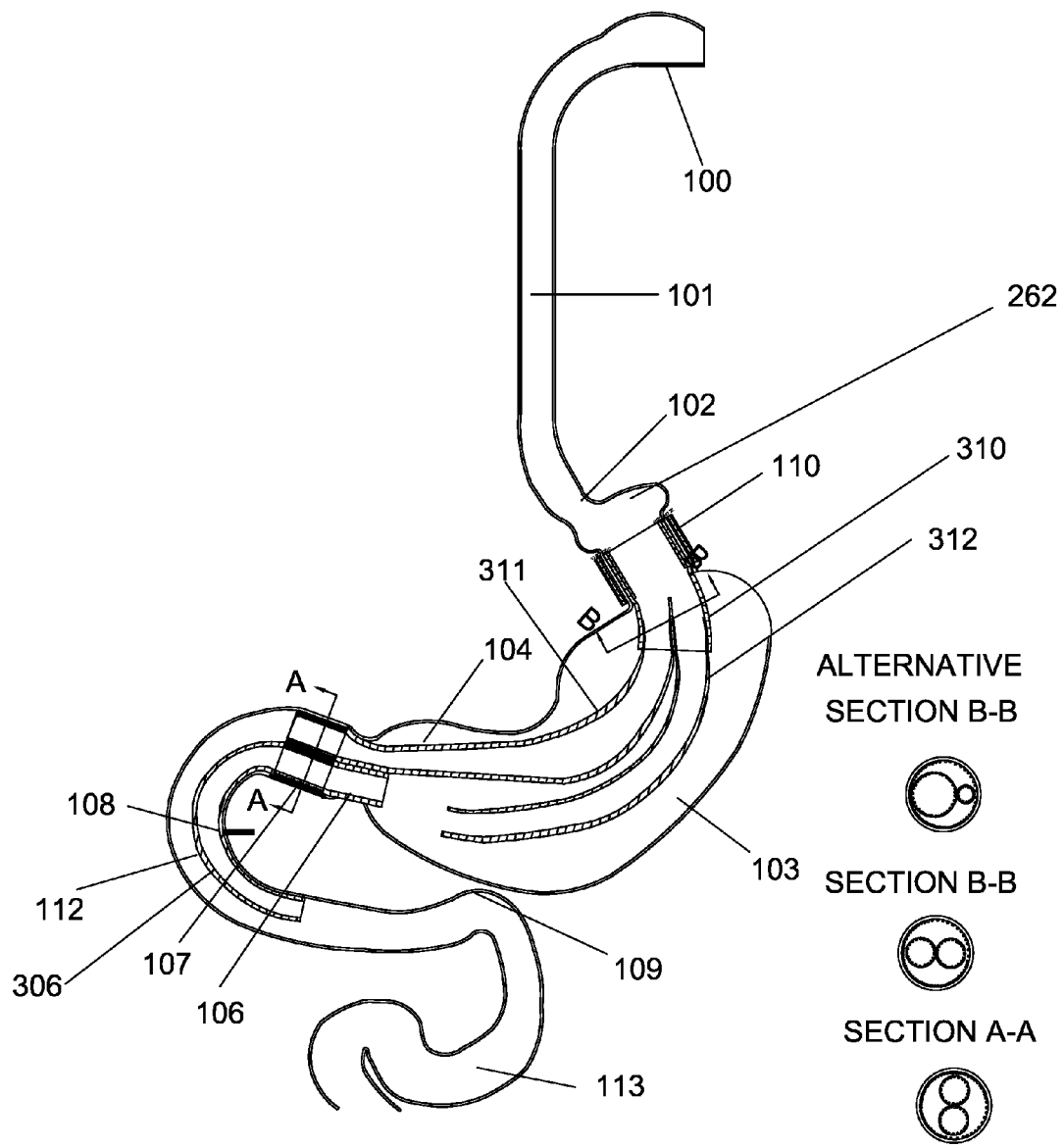
FIG. 19 is a sectional view of a portion of the digestive tract in the body. An external anchor is positioned around the outside of the esophagus. A bifurcated tubular implant (sleeve) is implanted on the inside of the esophagus and is anchored to the external anchor. A first branch of the bifurcated implant extends to an implant positioned in the duodenal bulb and a second branch extends into the stomach. A second tubular implant extends from the bifurcated tubular implant into the duodenum.

FIG. 19 shows a sectional view of a portion of the digestive tract in the body. As shown, an external band is implanted around the outside diameter of the esophagus (or alternatively a bifurcated implant is implanted inside). A bifurcated tubular implant 310 (sleeve) is implanted on the inside surface of the esophagus and anchored magnetically (or mechanically) through the esophageal tissue to the external band. A second tubular implant 311 extends from the bifurcated tubular implant 310 into the duodenum 112 to duodenal bulb 107. The band around the esophagus may form an optional restrictive stoma in the esophagus. A third sleeve 312 is implanted from the bifurcated tubular implant in the esophagus to the lower portion of the stomach near the stomach antrum or pylorus. A fourth sleeve 306 is implanted from the pylorus or stomach antrum to the middle or the end of the duodenum near the ligament of Treitz. As further described above, the two sleeves can each form a circular shape (or alternatively D shaped sections individually) in the overlap sections in the esophagus (or the duodenal bulb section). In some embodiments, the tubular implant 310 is formed in a branched (e.g., Y-shaped) configuration, having a proximal end adapted for coupling or anchoring in the esophagus and a distal portion including branches or limbs (e.g., sleeve 311 and sleeve 312). In other embodiments, the tubular implant 310 includes more than two branches (or limbs).

Various embodiments of the present invention shown and described above partial bypass elements where only part of the food bypasses the stomach (e.g., FIGS. 12-19). In these embodiments, there is an alternative flow path for food exiting the esophagus, such that if there is resistance to the passage of the food through the bypass sleeve element, the food has an alternative pathway to move forward. Such a configuration may help to reduce or eliminate dysphagia or dysphagia-like symptoms in a patient.

Figure 20:
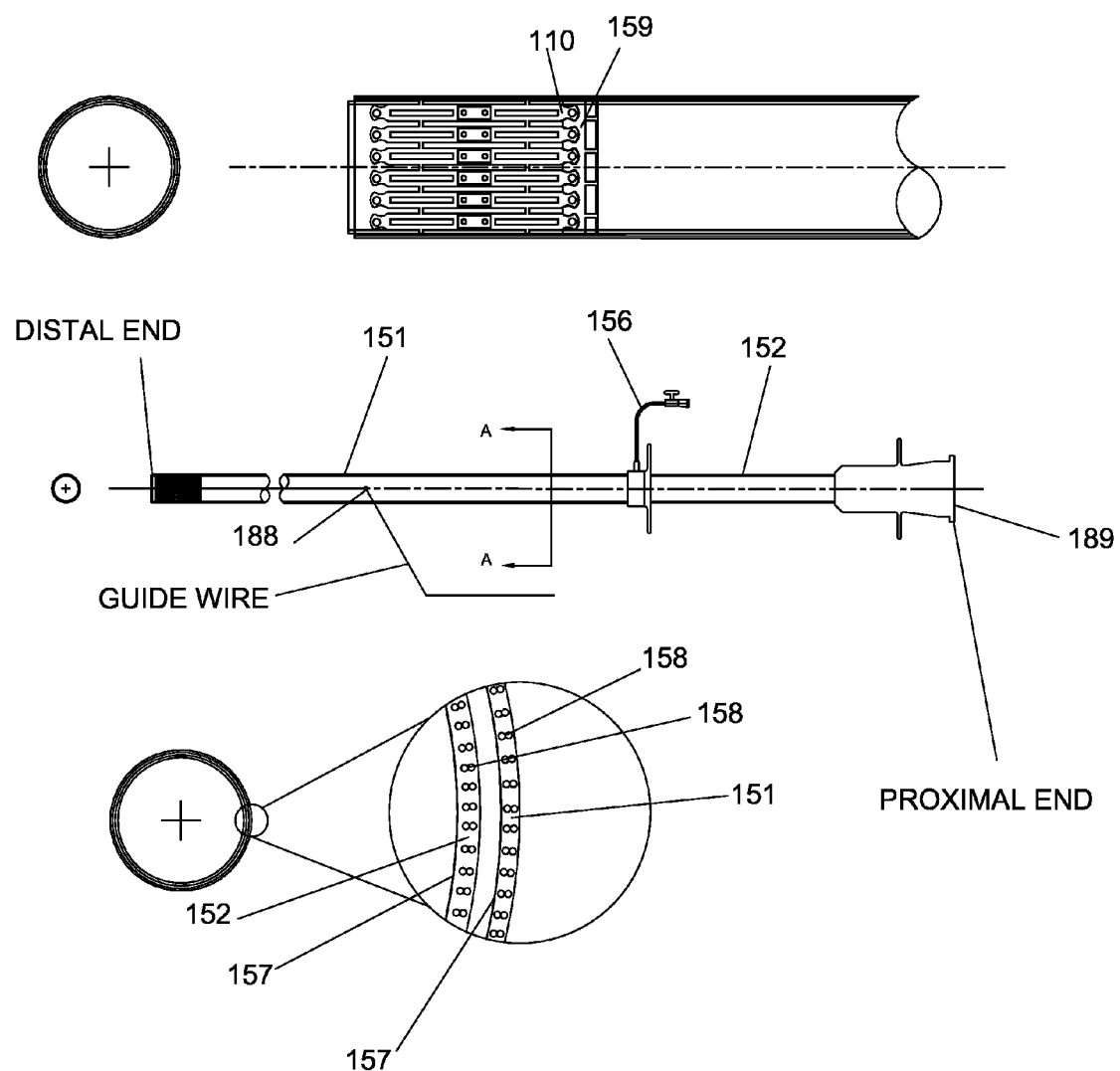
FIG. 20 is a schematic view of a delivery device for implanting an internal implant.

FIG. 20 shows a delivery catheter with an implant 110 loaded on to it for delivering a self-expanding internal tubular implant or stent. The catheter may be of an over-the-wire construction or a rapid exchange version. The delivery catheter is constructed with a smaller outside diameter to allow the catheter to be inserted through the working channel of the endoscope 114. The delivery catheter consists of an outer catheter 151 and an inner catheter 152. Attached to the inner catheter is a stent retainer 159. The purpose of the stent retainer 159 is to prevent the stent from releasing from the delivery catheter prematurely during deployment. The stent retainer is fastened to the inner catheter. The stent retainer 159 can be made from metal or plastic and can be made radio-opaque by making from it from a radio-opaque material such as tantalum. The stent retainer has a complementary shape that holds the tips on the stent and does not allow the stent to move distally or forward until the outer sheath 151 is fully retracted to the stent retainer 159. The catheter has a side port 156 which allows the space between the inner and outer sheaths to be flushed with saline. The outer sheath 151 and inner sheath 152 may be made from made from a simple single layer polymer extrusion such as from polyethylene or PTFE.

The outer sheath may also be constructed as follows. The sheath inner diameter surface is constructed of a thin wall PTFE liner 157. A layer of reinforcement 158 is placed over the PTFE liner. The reinforcement may be either a braid of wire or a coil of wire. The wire cross section can be either round or rectangular. The preferred material for the wire is a metal such as 316 or 304 stainless steel or Nitinol or other suitable material. The wire diameters are typically in the 0.0005 inch to 0.010 inch diameter range. The outer jacket material is preferably reflowed into the reinforcement layer by melting the material and flowing it into the spaces in between the braided wire or the coil wires. The outside diameter of this catheter will range typically from 1 mm to 4 mm. The catheter can be constructed to be an over the wire catheter or a rapid exchange catheter. For a rapid exchange design, the guide wire will enter the central lumen of the distal end of the catheter and exit at point 188. For an over-the-wire design, the guide wire will enter the central lumen of the distal end of the catheter and exit at point 189.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A modular gastrointestinal implant system for treating metabolic disorders such as diabetes and obesity by creating partial internal bypasses of food and organ secretions within the gastro-intestinal tract, the system comprising:
   an anchoring element configured for engaging an esophagus, the anchoring element having a docking feature;
   a first gastrointestinal implant having a coupling feature for engaging and coupling with the docking feature of the anchoring element and sized and shaped to extend from the esophagus to the duodenal bulb;
   wherein the docking feature and coupling feature are configured such that the first gastrointestinal implant may releasably couple with the anchoring element to facilitate removal of the first gastrointestinal implant; and
   a second gastrointestinal implant adapted to extend from the stomach or the duodenal bulb into the duodenum;
   wherein at least a portion of the first gastrointestinal implant extends laterally adjacent to at least a portion of the second gastrointestinal implant within the duodenal bulb.

2. The system of claim 1 wherein the anchoring element is an expandable stent.

3. The system of claim 1 wherein the anchoring element is a band and the docking feature includes one or more magnetic elements.

4. The system of claim 1 wherein the docking feature consists of a hook or loop fastener element and the coupling feature consists of a complementary hook or loop fastener element that enables attachment of the first gastrointestinal implant to the anchoring element.

5. The system of claim 1 wherein the docking feature includes a first mechanical element and the coupling feature includes a second mechanical element, and wherein the first and second mechanical elements are adapted to interlock.

6. The system of claim 1 wherein the first and second gastrointestinal implants are thin tubular sleeves.

7. The system of claim 1 wherein the first gastrointestinal implant is a Y-shaped sleeve having a first end with a single proximal branch and a second end including at least a first distal branch and a second distal branch.

8. The system of claim 7 further comprising a second anchoring element adapted for securing at the gastro-intestinal junction and for coupling with both the first and the second gastrointestinal implants.

9. The system of claim 8 wherein a proximal portion of the first gastrointestinal implant is connected to the anchoring element at the gastro-esophageal junction, the first distal branch is coupled to the second anchoring element, and the second distal branch is adapted to drain into the stomach.

10. The modular system of claim 1 wherein one end of the first gastrointestinal implant is connected to the docking feature, which comprises multiple segments, at the gastrointestinal junction and another end of the first gastrointestinal implant or the second gastrointestinal implant extends farther down the duodenum.

11. A modular gastrointestinal implant system for treating metabolic disorders such as diabetes and obesity by creating partial internal bypasses of food and organ secretions within the gastro-intestinal tract, the system comprising:
   a first anchoring element configured for engaging an esophagus, the first anchoring element having a docking feature;
   a second anchoring element configured for engaging a duodenum;
   a first gastrointestinal implant having a proximal end including a coupling feature for engaging the docking feature of the first anchoring element and a distal end adapted to couple with the second anchoring element;
   wherein the docking feature and coupling feature are configured such that the first implant may releasably couple with the first anchoring element to facilitate removal of the first gastrointestinal implant; and
   a second gastrointestinal implant adapted to extend from the stomach or the duodenal bulb into the duodenum, the second gastrointestinal implant adapted to couple with the second anchoring element;
   wherein at least a portion of the first gastrointestinal implant extends laterally adjacent to at least a portion of the second gastrointestinal implant within the second anchoring element.

12. The system of claim 11 wherein the first anchoring element is an expandable stent.

13. The system of claim 11 wherein the first anchoring element is a band and the docking feature includes one or more magnetic elements.

14. A method of treating metabolic conditions such as diabetes and obesity, the method comprising:
   securing a first anchoring element to the esophagus, the first anchoring element having a docking feature;
   securing a second anchoring element to the duodenum;
   implanting a first gastrointestinal implant having a proximal end including a coupling feature for engaging the docking feature of the first anchoring element and a distal portion adapted to couple with the second anchoring element;
   releasably coupling the coupling feature of the first gastrointestinal implant with the docking feature of the first anchoring element and coupling the distal portion with the second anchoring element;
   implanting a second gastrointestinal implant adapted to extend from the stomach or the duodenal bulb into the duodenum, the second gastrointestinal implant adapted to couple with the second anchoring element;
   coupling the second gastrointestinal implant to the second anchoring element, such that at least a portion of the first gastrointestinal implant extends laterally adjacent to at least a portion of the second gastrointestinal implant within the second anchoring element.

15. The method of claim 14 wherein the coupling feature and the docking feature are each magnetic structures adapted for magnetically coupling the first gastrointestinal implant to the first anchoring element.

16. The method of claim 14 wherein the coupling feature and the docking feature are mechanical elements adapted to interlock without penetrating the gastrointestinal tract.

17. A gastrointestinal implant system for treating metabolic disorders such as diabetes and obesity by creating partial internal bypasses of food and organ secretions within the gastro-intestinal tract, the system comprising:
   a first gastrointestinal implant having a feature for engaging and coupling within the esophagus, the first implant sized and shaped to extend from the esophagus to the duodenal bulb; and
   a second gastrointestinal implant adapted to extend from the stomach or the duodenal bulb into the duodenum;

wherein at least a portion of the first gastrointestinal implant extends laterally adjacent to at least a portion of the second gastrointestinal implant within the duodenal bulb.

18. The system of claim 17 wherein the feature for engaging and coupling within the esophagus is an expandable stent.

19. The system of claim 17 wherein the feature for engaging and coupling within the esophagus includes a band and a docking feature having one or more magnetic elements.

* * * * *